United States Patent
Panova et al.

(10) Patent No.: US 7,507,560 B2
(45) Date of Patent: Mar. 24, 2009

(54) ENZYMATIC PRODUCTION OF MACROCYCLIC AMIDE OLIGOMERS

(75) Inventors: Anna Panova, Hockessin, DE (US); Robert Dicosimo, Chadds Ford, PA (US); Edward G. Brugel, Wilmington, DE (US); Wilson Tam, Boothwyn, PA (US)

(73) Assignee: E. I. du Pont de Nemours and Company, Wilm., DE (US)

( * ) Notice: Subject to any disclaimer, the term of this patent is extended or adjusted under 35 U.S.C. 154(b) by 361 days.

(21) Appl. No.: 11/269,997

(22) Filed: Nov. 9, 2005

(65) Prior Publication Data

US 2006/0148044 A1    Jul. 6, 2006

Related U.S. Application Data

(60) Provisional application No. 60/626,222, filed on Nov. 9, 2004.

(51) Int. Cl.
C12P 17/00 (2006.01)
C12P 17/16 (2006.01)
C12P 17/18 (2006.01)

(52) U.S. Cl. .................. 435/117; 435/118; 435/119
(58) Field of Classification Search ............... 435/117, 435/118, 119
See application file for complete search history.

(56) References Cited

U.S. PATENT DOCUMENTS

| | | | |
|---|---|---|---|
| 2,020,298 | A | 11/1935 | Carothers et al. |
| 3,309,343 | A | 3/1967 | Darnell et al. |
| 5,466,744 | A | 11/1995 | Evans et al. |
| 5,661,214 | A | 8/1997 | Brunelle et al. |
| 6,141,103 | A | 10/2000 | Pinaton et al. |
| 6,376,026 | B1 | 4/2002 | Correll et al. |
| 6,677,427 | B1 | 1/2004 | Cheng et al. |

FOREIGN PATENT DOCUMENTS

WO    WO 94/12652 A1    6/1994

OTHER PUBLICATIONS

U.S. Appl. No. 10/698,275, filed Oct. 31, 2003, Brugel et al.
Immobilization of Enzymes and Cells; Gordon F. Bickerstaff, Editor; Humana Press, Totowa, NJ, USA: 1997 (Book not Supplied).
Macosko, C., Fundamentals of Reaction Injection Molding, Hanser Publishers: New York, NY; Chapter 7 (1989) (Book not Supplied).
Brunelle, D.J., Synthesis and Polymerization of Cyclic Polyester Oligomers, in Modern Polyesters, Schiers. J. and Long, T.E., eds., Wiley & Sons, New York, NY, 2003 (Book not Supplied).
U. Klun et al., Electrospray Mass Spectrometry Determination of Linear and Cyclic Oligomers of Polaymide-6, Polymer, vol. 42:7095-7099, 2001.
Zaks et al., Enzymatic Catalysis in Nonaqueous Solvents, The Journal of Biological Chemistry, vol. 263(7):3194-3201, 1988.
Zaks et al., Enzyme-Catalyzed Processes in Organic Solvents, Proc. Natl. Acad. Sci., vol. 82:3192-3196, 1985.
Zaks et al., The Effect of Water on Enzyme Action in Organic Media, The Journal of Biological Chemistry, vol. 263(17):8017-8021, 1988.
Peter J. T. Tait et al., Rate of Ethylene Polymerization With the Catalyst System (N5-RC5H4)ZZRCL2-Methylaluminoxane, American Chemical Society, Chapter 6, pp. 78-119, 1992.
Falmai Binns et al., Enzymic Polymerisation of an Unactivated DIOL/DIACID System, J. Chem. Soc. Perkin Trans., vol. 1:899-904, 1993.
Romas J. Kazlauska et al., Biotransformations with Lipases, Biotechnology, $2^{nd}$ ed., vol. 8A, eds. H. J. Rehm et al., Wiley-VCH, Weinheim, Germany, p. 40-191, 1998.
Eugenia M. Brazwell et al., Biocatalytic Synthesis of Polymers. III. Formation of a High Molecular Weight Polyester Through Limitation of Hydrolysis by Enzyme-Bound Water and Through Equilibrium Control, J. Polym. Sci. Part A: Polym Chem., vol. 33:89-95, 1995.
Apurva K. Chaudhary et al., Biocatalytic Solvent-Free Polymerization to Produce High Molecular Weight Polyesters, Biotechnol. Prog., vol. 13:318-325, 1997.
Arie L. Gutman et al., Enzymatic Formation of Lactams in Organic Solvents, Tetrahedron Letters, vol. 33(27):3943-3946, 1992.
Youchun Yan et al., Efficient Water Removal in Lipase-Catalyzed Esterifications Using a Low-Boiling-Point Azeotrope, Biotechnology and Bioengineering, vol. 78(1):31-34, 2002.
Colja Laane et al., Rules for Optimization of Biocatalysis in Organic Solvents, Biotechnology and Bioengineering, vol. XXX:81-87, 1987.
Shimona Geresh et al., Enzymatic Syntheses of Alkyds, II: Lipase-Catalyzed Polytransesterification of Dichloroethyl Fumarate With Aliphatic and Aromatic Diols, Biotechnology and Bioengineering, vol. 37:883-888, 1991.
Hans R. Kricheldorf et al., Macrocycles, 17. The Role of Cyclization in Kinetically Controlled Polycondensations. 2. Polyamides, Macromolecules, vol. 34:8879-8885, 2001.
Arnaud Lavalette et al., Lipase-Catalyzed Synthesis of a Pure Macrocyclic Polyester From Dimethyl Terephthalate and Diethylene Glycol, Biomacromolecules, vol. 3(2):225-228, 2002.

*Primary Examiner*—Herbert J. Lilling

(57) ABSTRACT

Hydrolytic enzymes capable of catalyzing amidation reactions can be used to produce cyclic amide oligomers from diesters and diamines. The cyclic amide oligomers are useful for the production of higher molecular weight polyamides.

67 Claims, 1 Drawing Sheet

US 7,507,560 B2

ENZYMATIC PRODUCTION OF MACROCYCLIC AMIDE OLIGOMERS

This application claims the benefit of U.S. Provisional Application No. 60/626,222, filed Nov. 9, 2004.

FIELD OF THE INVENTION

The invention relates to enzymatic synthesis of cyclic amide oligomers. Specifically, hydrolytic enzymes are used to produce a variety of cyclic amide oligomers from various diesters and diamines.

TECHNICAL BACKGROUND

Chemical synthesis of polyamides is well-known in the art. However, chemical synthesis often has many undesirable characteristics including 1) the use of expensive or toxic chemical catalysts and reactants, 2) the production of excess waste, especially for processes requiring high dilutions with solvents, and 3) a lack of selectively necessary to produce the desired products in high purity.

Enzymatic synthesis of polyesters and polyamides has been demonstrated using a variety of hydrolytic enzymes (i.e., lipases, esterases, etc.). Enzymes and their typical substrates are nontoxic, and enzymatic processes usually offer higher selectivity, decreased waste generation, and faster catalytic rates under milder conditions when compared to traditional chemical synthesis. In particular, lipases (E.C. 3.1.1.3) have been used extensively for the synthesis of polyesters and/or polyester (amides) in the presence or absence of organic solvents (Chaudary et al., *Biotech Prog.* 13:318-325 (1997); Brazwell et al., *J. Polym. Sci. Part A: Polym Chem.* 33:89-95 (1995); Binns et al., *J. Chem. Soc. Perkin Trans.* 1:899-904 (1993); Geresh et al., *Biotech. Bioeng.,* 37:883-888 (1991); and WO 94/12652).

Chemical and/or enzymatic polymer synthesis typically results in the production of linear oligomers that can be used for traditional in-mold polymerization (i.e., reaction injection molding) for the formation of shaped products. However, in-mold polymerization using linear (polyester or polyamide) oligomers has some limitations. Upon in-mold polymerization, the end groups on the linear oligomers will produce unwanted byproducts during the reaction such as water (i.e., when reacting a carboxylic acid end group with a hydroxyl or amine end group) or organic alcohols such as methanol (i.e., when reacting an ester with a hydroxyl or amine end group). The unwanted byproducts typically need to be removed and may adversely affect the physical characteristics of the molded product. These adverse effects include increased void content and decreased surface finish quality. Lastly, linear oligomers tend to have high melt viscosities, which may limit the ability to form higher molecular weight polymers or may limit their use in the formation of finer moldable products.

Cyclic ester oligomers (CEOs) and cyclic amide oligomers (CAOs) offer a distinct processing advantage over the use of linear oligomers. First, cyclic oligomers do not introduce endgroups during polymerization. This allows materials to be prepared without the formation of volatiles in the in-mold polymerization process. Second, much higher molecular weight polymers can be prepared because the monomers lack end groups, which translates into polymers without many end groups. Third, cyclic oligomers typically have lower melt viscosities. The use of lower melt viscosity cyclic oligomer for in-mold polymerization (e.g., reaction injection molding) enables production of polymers having molecular weights typically not obtainable when using linear oligomers and allows formation of finer moldable parts.

Cyclic ester oligomers (CEOs) have been known for many years, see for instance U.S. Pat. No. 2,020,298. CEOs are known to be present in varying, usually small, quantities in many linear polyesters and have been isolated from such linear polyesters. They are often low viscosity liquids that may be polymerized to higher molecular weight linear polyesters by ring opening polymerization, see for instance U.S. Pat. Nos. 5,466,744 and 5,661,214 and references cited therein. Enzymatic synthesis of CEOs has previously been reported (U.S. Ser. No. 10/698,275, hereby incorporated by reference; Lavalette et al., *Biomacromolecules,* 3:225-228 (2002)).

Cyclic amide oligomers (CAOs) are normally produced during chemical polycondensation reactions. Kricheldorf et al. (*Macromolecules,* 34:8879-8885 (2001)) produced a variety of aliphatic and aromatic linear amide oligomers (LAOs) and CAOs by the chemical reaction of diamines or silylated diamines with dicarboxylic acid dichlorides. Kricheldorf et al. do not teach an enzymatic method for the production of cyclic amide oligomers.

WO 94/12652 describes a process for the production of polyesters or polyester (amides) in an enzyme-catalyzed reaction in the absence of added solvent, whereby the desired polyesters or polyesteramides are produced with high average molecular weight and narrow dispersity. For the production of polyester (amides), the reaction of at least one aliphatic dicarboxylic acid or derivative thereof with at least one aliphatic hydroxyamine, diol, polyol, diamine or polyamine, and optionally, at least one aliphatic hydroxycarboxylic acid, aminocarboxylic acid or derivative is described. The polyester or polyester (amide)s produced in this process have a most preferred acid number of about 1 (page 18, line 17), indicating that the products are linear polyester or polyester (amide) oligomers, and not cyclic polyester or polyester (amide) oligomers. In the case of polyester production, the production of up to 1.5% cyclic diester impurity is indicated as undesirable, and methods are provided for the removal of unwanted cyclic impurity (page 19, lines 1-15).

Recently, it has been reported that linear amide oligomers (LAOs) can be made from diesters and diamines using hydrolytic enzymes (e.g. lipases, esterases, proteases, etc.). Cheng et al. (U.S. Pat. No. 6,677,427) report an enzyme catalyzed process to prepare a variety of linear and/or branched polyamide oligomers by the reaction of a polyamine and diester in the presence of a hydrolytic enzyme obtained from species such as *Candida* (*Candida antartica*), *Pseudomonas* species (*Pseudomonas fluorescens*), or *Mucor* species (*Mucor miehei*). Cheng et al. do not report the formation of cyclic amide oligomers. Specifically, Cheng et al. state in column 13, lines 2-4, "Although the polyamides may be linear or branched, the polyamides of the present invention are preferably linear and have a narrow molecular weight polydispersity ($M_w/M_n$)", and in column 6, lines 20-21, "The polyamides of the present invention may have residues of at least one diester and at least one polyamine". The polyamides described in Cheng et al. generally have a molecular weight range from about 4,000 to 12,000 Daltons (column 6, line 29), indicating that high molecular weight linear polyamides were formed. The process of Cheng et al. was performed without added solvent, or optionally in the presence of at least one protic solvent such as methanol, ethanol, ethylene glycol, glycerol, t-butanol, isopropanol, or in a water/salt mixture such as water/NaCl (column 4, lines 26-31); preferably, the reaction was performed in the absence of solvent (column 8, lines 37-39; column 10, lines 52-57; Example 1, lines 17-19; Examples 3-5). All of the working examples were conducted in the absence of solvent at essentially equimolar amounts of the diester and polyamine, where the concentration of each substrate was in excess of about 2.75 molar. Completion of each reaction was generally determined by the formation and characterization of a solid product.

Gutman et al. (*Tetrahedron Lett.*, 33(27):3943-3946 (1992)) describe the use of porcine pancreatic lipase to catalyze the formation of macrocyclic bislactams from diesters and diamines and found that no reaction occurs in the absence of enzyme, and that in the presence of enzyme the reaction proceeds only when employing the activated monochloroethyl diester, but not with the ethyl diester or the free dicarboxylic acid (p 3944, last paragraph). Gutman et al. teaches that the enzymatic production of macrocyclic bislactams requires that the alkoxy leaving group of the diester be activated (e.g. 2-chloroethyoxy), whereas in the present invention the diesters employed in the production of cyclic amide oligomers (CAOs) can have unactivated alkoxy leaving groups (e.g., methoxy, ethoxy).

The problem to be solved is to provide a method for the enzymatic synthesis of cyclic amide oligomers from non-activated diesters and diamines.

SUMMARY OF THE INVENTION

The stated problem has been solved by providing a process for the enzymatic synthesis of cyclic amide oligomers from non-activated diester and diamines comprising the steps of:
(a) contacting,
i) at least one diester of the general formula

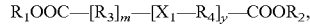

$R_1OOC-[R_3]_m-[X_1-R_4]_y-COOR_2$, wherein $R_1$ and $R_2$ are independently a C1 to C20 hydrocarbyl group selected from one of alkyl, alkylene, aryl, haloaryl, aralkyl, aralkylene, arylene, alkoxyalkyl, and alkenyl, optionally substituted with one or more ether linkages; m is 0 to 1; $R_3$ and $R_4$ are independently C1 to C10 hydrocarbyl group selected from one of alkyl, alkylene, aryl, haloaryl, aralkyl, aralkylene, arylene, and alkenyl; and $X_1$ is selected from one or none of heteroatom or non-heteroatom, wherein the heteroatom comprises oxygen, and wherein the non-heteroatom comprises NH; y is 0 to 5; wherein m is 1 when $X_1$ is a heteroatom or non-heteroatom; and (ii) at least one diamine of the general formula

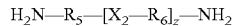

$H_2N-R_5-[X_2-R_6]_z-NH_2$ wherein $R_5$ and $R_6$ are C1 to C6 hydrocarbyl group selected from the group consisting of alkyl, akylene, aryl, haloaryl, aralkyl, aralkylene, alkarylene, arylene, and alkenyl; $X_2$ is selected from one or none of heteroatom or non-heteroatom, wherein the heteroatom comprises oxygen or sulfur, and wherein the non-heteroatom comprises amine, carbonyl, or C1 to C6 hydrocarbyl group selected from one of alkyl, alkylene, aryl, haloalkyl, aralkyl, aralkylene, arylene or alkenyl; z is from 0 to 20; and wherein $R_5$ and $R_6$ may be the same or different;

under a set of suitable reaction conditions, in a medium comprised of at least one aprotic organic solvent, and in the presence of a lipase having a cyclic amide oligomer synthesizing activity and present in an amount of at least about 0.01% by weight based on the total weight of the diester and diamine whereby a cyclic amide oligomer is produced;

(b) recovering an amount of cyclic amide oligomer from the reaction of step (a).

In one embodiment, $R_1$ and $R_2$ are independently a C1 to C6 hydrocarbyl group optionally substituted with one or more ether linkages; m is 0 or 1; $R_3$ is C1 to C10 hydrocarbyl group; y is 0 to 5; $R_4$ is a C1 to C3 hydrocarbyl group; $R_5$ and R6 are independently C1 to C6 hydrocarbyl group; z is 0 to 5; and $X_2$ is one or none of heteroatom or non-heteroatom, wherein the heteroatom comprises oxygen or sulfur, and wherein the non-heteroatom comprises amine, carbonyl, or C1 to 4 hydrocarbyl group.

In another embodiment, $R_1$ and $R_2$ are independently a C1 to C6 alkyl group optionally substituted with one or more ether linkages; m is 1; $R_3$ is C1 to C10 alkyl group; y is 0; $R_5$ and $R_6$ are independently is C1 to C6 hydrocarbyl group; z is 0 to 4; and $X_2$ is one or none of heteroatom or non-heteroatom, wherein the heteroatom comprises oxygen or sulfur, and wherein the non-heteroatom comprises amine, carbonyl, or C1 to 4 hydrocarbyl group.

In a further embodiment, $R_1$ and $R_2$ are independently a C1 to C6 alkyl group optionally substituted with an ether linkage; m is 1; $R_3$ is C1 to C10 alkyl group; y is 0; $R_5$ is C1 to C6 hydrocarbyl group; z is 0 to 4; $R_6$ is a C1 to C4 alkyl group; $X_2$ is one or none of heteroatom or non-heteroatom, wherein the heteroatom is oxygen, and wherein the non-heteroatom is amine or C1 to C4 alkyl group.

In yet another embodiment, $R_1$ and $R_2$ are independently a C1 to C2 alkyl group; m is 1; $R_3$ is C1 to $C_{10}$ alkyl group; y is 0; $R_5$ is C1 to C6 alkyl group; z is 1; $R_6$ is a C1 to C4 alkyl group; and $X_2$ is C1 to C2 alkyl group.

The enzyme catalyst is an unimmobilized or immobilized lipase obtained from a natural or synthetic source. In one embodiment, the lipase is obtained from a plant, animal, bacteria, yeast, or fungi. In another embodiment, the lipase is obtained from a natural source selected from the group consisting of *Pseudomonas, Burkholderia, Mucor, Alcaligenes*, and *Candida*. In yet another embodiment, the natural source of the lipase is *Alcaligenes* sp., *Mucor miehei, Psuedomonas* sp., *Pseudomonas cepacia*, and *Burkholderia cepacia*, and *Candida antartica*. In a further embodiment the lipase is selected from the group consisting of *Candida antartica* lipase B, *Alcaligenes* sp. lipase, *Mucor miehei* lipase, *Pseudomonas* sp. lipase, *Pseudomonas cepacia* lipase, and *Burkholderia cepacia* lipase. In yet a further embodiment, the lipase is selected from the group consisting of *Candida antartica* lipase B (Novozym® 435), *Alcaligenes* sp. lipase (Bio-Catalytics ICR-117), *Alcaligenes* sp. lipase (Boehringer Mannheim #1859366) *Mucor miehei* lipase (BioCatalytics ICR-116), *Pseudomonas* sp. lipase (Biocatalytics ICR-113), *Pseudomonas* sp. lipase (BioCatalytics ICR-129), *Pseudomonas cepacia* lipase (Boehringer Mannehim #1827642), *Burkholderia cepacia* lipase (Amano PS-C Amano I) and *Burkholderia cepacia* lipase (Amano PS-C Amano II). In a preferred embodiment, the lipase is *Candida antartica* lipase B.

Suitable diesters include, but are not limited to dialkyl adipate, dialkyl malonate, dialkyl succinate, dialkyl glutarate, dialkyl phthalate, dialkyl isophthalate, dialkyl terephthalate, dialkyl maleate, dialkyl fumarate, dialkyl oxalate, dialkyl phenylmalonate, dialkyl suberate, dialkyl sebacate, bis(2-butoxyethyl)adipate, dimethyl 2,2'-oxybisacetate, dimethyl 3,3'-oxybispropanoate, dimethyl 3,3'-[1,2-ethanediylbis (oxy)]bispropanoate, and β-alanine, N-(3-methoxy-3-oxopropyl) methyl ester, and mixtures thereof.

Suitable diamines include, but are not limited to 1,6 diaminohexane, 1,12-diamino dodecane, 1,10-diaminodecane, diethylenetriamine, triethyleneglycol diamine, ethylenediamine, propylenediamine, triethylenetetramine, dipropylenetriamine, tripropylenetetramine, tetrapropylenepentamine, spermine, bis-(hexamethylenetriamine), o-phenylenediamine, poly(oxyethylene)diamine, poly(oxypropylene)diamine, polyetherdiamine, and mixtures thereof.

Suitable aprotic solvents include, but are not limited to o-dichlorobenzene, diphenyl ether, chlorobenzene, methyl-tert-butyl ether, di-isopropyl ether, tetrahydrofuran, acetone, acetonitrile, 1,4-dioxane, N,N-dimethylformamide, dimethyl sulfoxide, 1,1,1-trichloroethane, dichloroethane, toluene, xylenes, cyclohexane, heptane, isooctane, perchloroethylene, a molar excess of the diamine, a molar excess of the diester, and mixtures thereof.

In another aspect, a process for the production of cyclic amide oligomers from linear amide oligomers is provided comprising the steps of:

(a) contacting, in the presence of a lipase having a cyclic amide oligomer synthesizing activity under a set of suitable reaction conditions, at least one linear amide oligomer of the general formula $$(A-B)_n;$$

wherein n=1 to 20; A is derived from a diester having the general formula:

$$R_1OOC—[R_3]_m—[X_1—R_4]_y—COOR_2,$$

wherein $R_1$ and $R_2$ are independently C1 to C20 hydrocarbyl group selected from one of alkyl, alkylene, aryl, haloaryl, aralkyl, aralkylene, arylene, alkoxyalkyl, and alkenyl, optionally substituted with one or more ether linkages; m is 0 or 1; $R_3$ and $R_4$ are independently C1 to C10 hydrocarbyl group selected from one of alkyl, alkylene, aryl, haloaryl, aralkyl, aralkylene, arylene, and alkenyl; $X_1$ is selected from one or none of heteroatom or non-heteroatom, wherein the heteroatom comprises oxygen, and wherein the non-heteroatom comprises NH; and y is 0 to 5; wherein m is 1 when $X_1$ is a heteroatom or non-heteroatom, and B is derived from a diamine having the general formula:

$$H_2N—R_5—[X_2—R_6]_z—NH_2;$$

wherein $R_5$ and $R_6$ are C1 to C6 hydrocarbyl group selected from the group consisting of alkyl, akylene, aryl, haloaryl, aralkyl, aralkylene, alkarylene, arylene, and alkenyl; $X_2$ is selected from one or none of heteroatom or non-heteroatom, wherein the heteroatom comprises oxygen or sulfur, and wherein the non-heteroatom comprises amine, carbonyl, or C1 to C6 hydrocarbyl group selected from one of alkyl, alkylene, aryl, haloalkyl, aralkyl, aralkylene, arylene or alkenyl; z is from 0 to 20; and wherein $R_5$ and $R_6$ may be the same or different; under a set of suitable reaction conditions, in a medium comprised of at least one aprotic organic solvent, in the presence of a lipase enzyme having a cyclic amide oligomer synthesizing activity and present in an amount of at least about 0.01% by weight based on the total weight of the diester and diamine, whereby a cyclic amide oligomer is produced;

(b) recovering an amount of cyclic amide oligomer from the reaction of step a).

In a further aspect, the invention includes a method to form shaped articled by polymerize a cyclic amide oligomer comprising:

a) providing at least one cyclic amide oligomer; and
b) polymerizing said cyclic amide oligomer in a process selected from the group consisting of injection molding, rotational molding, resin film infusion, resin transfer molding, filament winding, a powder coating process to create a prepeg or film, hot melt prepeg preparation, compression molding, roll wrapping, and pultrusion; whereby a shaped article is produced.

In another embodiment, the invention includes shaped articles formed by polymerizing a cyclic amide oligomer using a process selected from the group consisting of injection molding, rotational molding, resin film infusion, resin transfer molding, filament winding, a powder coating process to create a prepeg or film, hot melt prepeg preparation, compression molding, roll wrapping, and pultrusion.

Articles so formed include automotive body panels, automotive chassis components, bumper beams, aircraft wing skins, windmill blades, fluid storage tanks, tractor fenders, tennis rackets, golf club shafts, windsurfing masts, toys, rods, tubes, bars stock, bicycle forks, films, coatings, encapsulated wires, and machine housings.

BRIEF DESCRIPTION OF THE DRAWINGS

The invention can be more fully understood from the Figure and the detailed description that together form this application.

In FIG. 1, cU % means mole percent cyclic unimer, cD % means mole percent cyclic dimer, and CAO % means mole percent of total cyclic amide oligomers formed.

DETAILED DESCRIPTION OF THE INVENTION

Figure 1:
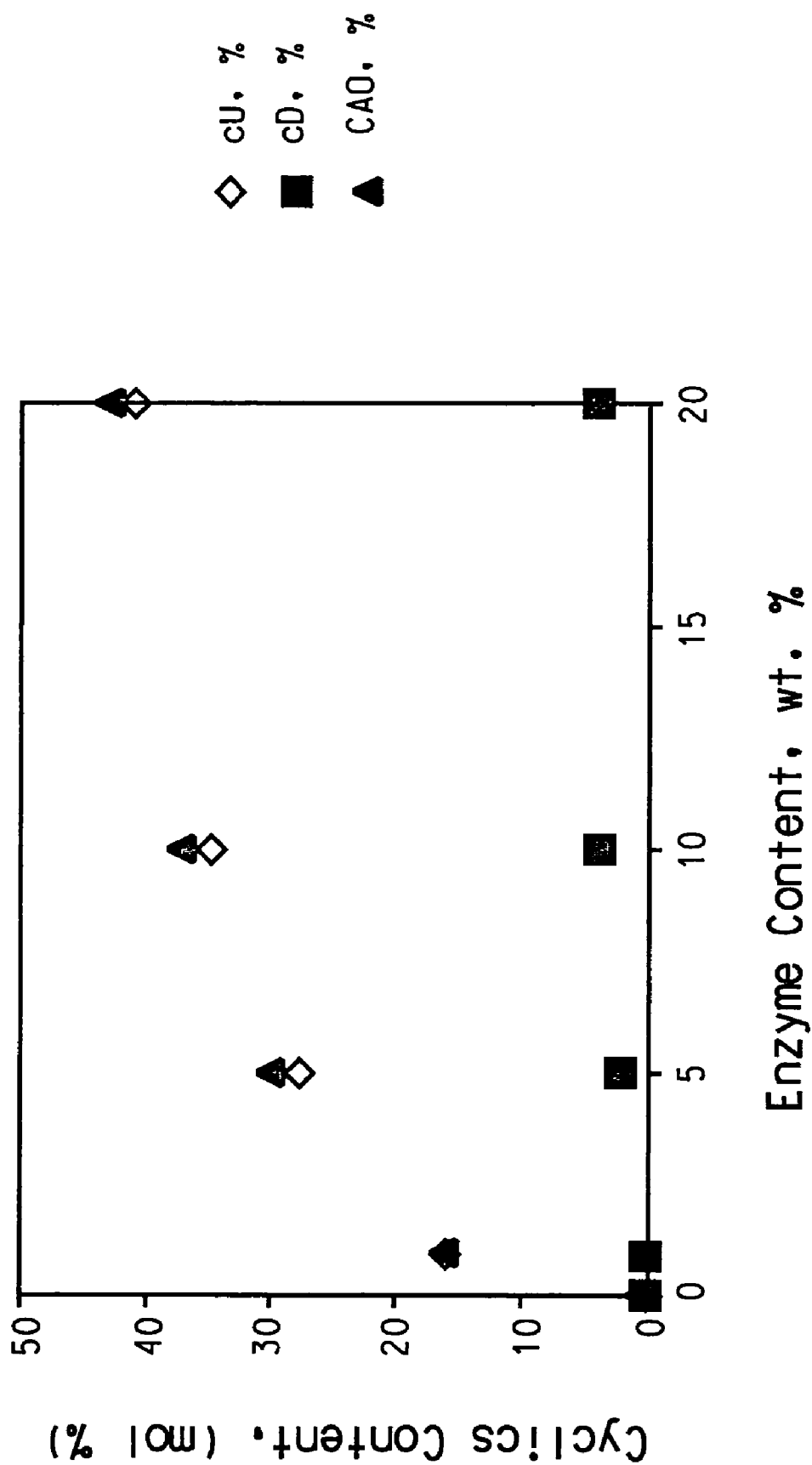
FIG. 1 shows the effect of enzyme catalyst weight percent on cyclic amide oligomer synthesis (also see Example 6 and Table 5).

An enzymatic process is provided for the synthesis of cyclic amide oligomers (CAOs) in relatively high yield from non-activated diesters and diamines under mild reaction conditions. The isolated CAOs may be used for ring opening polymerization reactions in applications, such as reaction injection molding, to create high molecular weight polyamides.

In this disclosure, a number of terms and abbreviations are used. The following definitions are provided:

As used herein, the term "comprising" refers to the presence of the stated features, integers, steps, or components as referred to in the claims, but that it does not preclude the presence or addition of one or more other features, integers, steps, components or groups thereof.

As used herein, the term "diester" is used to describe an aliphatic or aromatic compound containing at least two ester groups and is described by the formula:

$$R_1OOC—[R_3]_m—[X_1—R_4]_y—COOR_2$$

wherein $R_1$ and $R_2$ are independently C1 to C20 hydrocarbyl group selected from one of alkyl, alkylene, aryl, haloaryl, aralkyl, aralkylene, arylene, alkoxyalkyl, and alkenyl, optionally substituted with one or more ether linkages; m is 0 to 1; $R_3$ and $R_4$ are independently C1 to C10 hydrocarbyl group selected from one of alkyl, alkylene, aryl, haloaryl, aralkyl, aralkylene, arylene, alkenyl, and mixtures thereof; $X_1$ is selected from one or none of heteroatom or non-heteroatom, wherein the heteroatom comprises oxygen, and wherein the non-heteroatom comprises NH; y is 0 to 5; wherein m is 1 when $X_1$ is a heteroatom or non-heteroatom.

Examples of suitable diesters include, but are not limited to dialkyl adipate, dialkyl malonate, dialkyl succinate, dialkyl glutarate, dialkyl o-phthalate, dialkyl isophthalate, dialkyl terephthalate, dialkyl maleate, dialkyl fumarate, dialkyl oxalate, dialkyl phenylmalonate, dialkyl suberate, dialkyl sebacate, bis(2-butoxyethyl)adipate, dimethyl 2,2'-oxybisacetate, dimethyl 3,3'-oxybispropanoate, dimethyl 3,3'-[1,2-ethanediylbis(oxy)]bispropanoate, and β-alanine, N-(3-methoxy-3-oxopropyl), methyl ester, or mixtures thereof. In another embodiment, diesters include dialkyl malonate, dialkyl succinate, dialkyl oxalate, dialkyl suberate, dialkyl sebacate, and bis(2-butoxyethyl)adipate.

As used herein, the term "diamine" is used to describe an aliphatic or aromatic compound having at least two amine groups and is described by the formula:

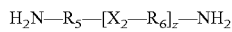

wherein $R_5$ and $R_6$ are C1 to C6 hydrocarbyl group selected from the group consisting of alkyl, akylene, aryl, haloaryl, aralkyl, aralkylene, alkarylene, arylene, and alkenyl; $X_2$ is selected from one or none of heteroatom or non-heteroatom, wherein the heteroatom comprises oxygen or sulfur, and wherein the non-heteroatom comprises amine, carbonyl, or C1 to C6 hydrocarbyl group selected from one of alkanol, alkyl, alkylene, aryl, haloaryl, aralkyl, aralkylene, arylene or alkenyl; z is from 0 to 20; and wherein $R_5$ and $R_6$ may be the same or different.

In one embodiment, examples of suitable diamines include, but are not limited to 1,6-diaminohexane (hexamethylenediamine), 1,12-diaminododecane, 1,10-diaminodecane, diethylenetriamine, triethyleneglycol diamine, ethylenediamine, propylenediamine, triethylenetetramine, dipropylenetriamine, tripropylenetetramine, tetrapropylenepentamine, spermine, bis-(hexamethylenetriamine), O-phenylenediamine, poly(oxyethylene)diamine, poly(oxypropylene)diamine, polyetherdiamine, and mixtures thereof. In another embodiment, diamines include ethylenediamine, 1,6-diamohexane, 1,12-diaminododecane, triethyleneglycol diamine, and o-phenylenediamine.

As used herein, the term "aromatic diester" means an organic compound that includes an aromatic ring as a part of its structure and has at least two ester groups. The aromatic diester may be substituted with one or more functional groups such as ether, thioether, and oxo (keto) that do not substantially interfere with the various reactions described in the processes herein.

As used herein, the term "aliphatic diester" means an organic compound, typically linear or branched in structure, which does not have an aromatic ring as part of its structure and has at least two ester groups. The aliphatic diester may be substituted with one or more functional groups such as ether, thioester, and oxo (keto) that do not substantially interfere with the various reactions described in the methods herein.

As used herein, the term "aromatic diamine" means an organic compound that includes an aromatic ring as a part of its structure and has at least two amine groups. The aromatic diamine may be substituted with one or more functional groups such as halogen, ether, thioether, amine, and oxo (keto) which do not substantially interfere with the various reactions described in the processes herein. Typically, the aromatic diamine is comprised of two primary amine groups.

As used herein, the term "aliphatic diamine" means an organic compound, typically linear or branched in structure, which does not have an aromatic ring as part of its structure and has at least two amine groups. The aliphatic diamine may be substituted with one or more functional groups such as ether, thioester, amine, and oxo (keto) that do not substantially interfere with the various reactions described in the methods herein. Typically, the aliphatic diamine is comprised of two primary amine groups.

As used herein, the term "hydrocarbyl" refers to aliphatic, cycloaliphatic or aromatic groups comprising carbon and hydrogen. The hydrocarbyl groups are comprised of alkyl, alkylene, aryl, haloaryl, aralkyl, aralkylene, alkarylene, arylene, and alkenyl groups. Hydrocarbyl is understood to include saturated or unsaturated, cyclic, branched or linear, substituted hydrocarbyl groups with the latter referring to the hydrocarbon portion bearing additional substituents such as oxygen (e.g. ether linkages). Examples of hydrocarbyl groups include, but are not limited to methyl, ethyl, propyl, isopropyl, butyl, isobutyl, t-butyl, cyclopropyl, cyclobutyl, cyclopentyl, methylcyclopentyl, cyclohexyl, methylcyclohexyl, benzyl, phenyl, o-tolyl, m-tolyl, p-tolyl, xylyl, vinyl, allyl, butenyl, cyclohexenyl, cyclooctenyl, cyclooctadienyl, and butynyl.

As used herein, the term "heteroatom" refers to an atom other than carbon including, but not limited to, S or O. As used herein, the term "non-heteroatom" refers to atoms including, but not limited to amine, carbonyl, and hydrocarbyl groups.

As used herein, the term "substituted" means a group that is substituted and contains one or more substituent groups that do not cause the compound to be unstable or unsuitable for the use or reaction intended. Substituent groups which are generally useful include nitrile, ether, ester, halo, amino (including primary, secondary and tertiary amino), hydroxy, oxo, vinylidene or substituted vinylidene, silyl or substituted silyl, nitro, nitroso, sulfinyl, sulfonyl, sulfonic acid alkali metal salt, boranyl or substituted boranyl, and thioether.

As used herein, an "oligomer" means a molecule that contains at least one identifiable structural repeat unit of the same formula.

As used herein, the terms "cyclic amide oligomer", "CAO", "macrocyclic polyamide", and "MPA" are used interchangeably to describe a cyclic compound with at least two amide bonds derived from a diester and a diamine. The cyclic amide oligomers of the present invention have the following general formula:

wherein the A is derived from a diester; B is derived from a diamine; and n is typically from about 1 to about 20, preferably about 1 to about 15, more preferably about 1 to about 5, and most preferably from about 1 to about 3. The cyclic amide oligomer formed when n=1 is also known as the cyclic unimer. A similar naming convention is used to described the cyclic amides formed when n=2 (cyclic dimer), n=3 (cyclic trimer), n=4 (cyclic tetramer), etc. The cyclic amide oligomers reported in the present examples are typically unimers, dimers, and trimers; however larger cyclic amide oligomer structures may be produced using the present methods. In one embodiment, at least about 1 mole percent (mol %), more preferably at least about 5 mole percent, even more preferably at least about 25 mole percent, and most preferably at least about 50 mol percent of the substrates (e.g. based on diester and diamine used) are converted into the corresponding cyclic amide oligomer.

As used herein, the term "enzyme catalyst" refers to a catalyst that is characterized by cyclic amide oligomer-forming activity. The lipases described herein have been found to have cyclic amide oligomer-forming activity. As used herein, "cyclic amide oligomer-forming activity" refers to a enzyme (i.e. lipase) having the ability to catalyze the formation of cyclic amide oligomers under the reaction conditions described herein. Certain combinations of diester and diamines react in the absence of an enzyme catalyst to produce cyclic amide oligomers under the reaction conditions described herein (Table 10). However, the addition of an enzyme catalyst under the same reaction conditions greatly increased the molar percent of total cyclic amide oligomer formed. In one embodiment, the present enzyme catalysts increase the molar percent of total cyclic amide oligomer formed (CAO %) at least about 1.5 fold relative to the amount of cyclic amide oligomer formed in the absence of the enzyme catalyst under identical reaction conditions.

The enzyme catalyst may be in the form of a whole microbial cell, permeabilized microbial cell(s), one or more cell components of a microbial cell extract, partially purified enzyme, or purified enzyme. The enzyme catalyst may be used in an unimmobilized form or may be immobilized on a soluble or insoluble support using methods well-known to those skilled in the art; see for example, *Immobilization of Enzymes and Cells*; Gordon F. Bickerstaff, Editor; Humana Press, Totowa, N.J., USA; 1997. The use of immobilized enzymes permits the recovery and reuse of the catalyst in subsequent reactions. Supports may include materials such as diatomaceous earth, polysaccharides (i.e., chitosan, alginate or carrageenan), titania, silica, alumina, polyacrylates and polymethacrylates, polyurethanes and ion exchange resins, and the enzyme may be adsorbed, covalently attached, or ionically attached, or in the form of crosslinked enzyme crystals (CLECS).

As used herein, the term "lipase" refers to any enzyme having lipase activity. As used herein, "lipase activity" refers to the enzymatic activity associated with the hydrolysis of fats into glycerol and fatty acids by hydrolyzing ester bonds. Hydrolytic enzymes having lipase activity also include proteases, amidases, and esterases. Lipases also have the ability to catalyze the synthesis of polymers, such as polyesters and polyamides, via the formation of ester (i.e. transesterification) and amide (i.e. transamidation) bonds; respectively. In one embodiment, lipases useful in present invention are those having the ability to catalyze the synthesis of cyclic amide oligomers. In another embodiment, lipases useful in the present invention are those that increase the molar percent of total cyclic amide oligomer formed (CAO %) at least about 1.5 fold relative to the amount of cyclic amide oligomer formed in the absence of the enzyme catalyst under identical reaction conditions.

Many lipases have been reported (see the chapter by R. J. Kazlauskas et al., *Biotransformation with Lipases*, in Biotechnology, $2^{nd}$ Ed, Vol. 8a, Eds. H. J. Rehm et al., Wiley-VCH, Weinheim, Germany, p. 40-191 (1998)). In one embodiment, lipases suitable for use in the present methods can be obtained from natural sources such as animals, plants, bacteria, yeast, fungi or virus, or from synthetic sources. In one embodiment, natural sources of suitable lipases include *Alcaligenes* species, *Candida* species (*Candida antartica* lipase B), *Pseudomonas* species, *Mucor* species (e.g., *Mucor miehei*), and *Burkholderia* species (e.g. *Burkholderia cepacia*, formerly known as *Pseudomonas cepacia*). In yet another embodiment, the lipase is selected from the group consisting of *Alcaligenes* sp. lipase, *Mucor miehei* lipase, *Pseudomonas* sp. lipase, *Burkholderia cepacia* lipase, and *Candida antartica* lipase B. In a further embodiment, the lipase is obtained from a commercially available source. In yet a further embodiment, the lipase is selected from the group consisting of *Alcaligenes* sp. lipase (BioCatalytics, Inc., ICR-117), *Mucor miehei* lipase (BioCatalytics, Inc., ICR-116), *Pseudomonas* sp. lipase (BioCatalytics, Inc., ICR-113 or ICR-129), *Burkholderia cepacia* lipase (Amano Enzymes, Inc., PS-C Amano I and PS-C Amano II), and *Candida antartica* lipase B (Novozymes A/S, immobilized on an acrylic resin; Novozym® 435). In one aspect, particularly useful catalysts are *Candida antartica* lipase B (Novozym® 435) and *Pseudomonas* sp. lipase (BioCatalytics, Inc. ICR-113, ICR-129). In another aspect, suitable lipases include *Alcaligenes* sp. lipase (Boehringer Mannheim, # 1859366) and *Pseudomonas cepacia* lipase (Boehringer Mannheim, #1827642). In a further aspect, immobilized catalysts include *Candida antartica* lipase B (Novozym® 435) and immobilized *Pseudomonas* sp. lipase (ICR-129, BioCatalytics, Inc).

The concentration (w/v percent) of the enzyme, either unimmobilized or immobilized, preferably ranges from about 0.01 weight percent (wt %) to about 25 wt %, more preferably about 1 wt % to about 10 wt %, and most preferably from 3 wt % to about 10 wt % based on the total weight of the reaction mixture. The specific activity of the unimmobilized enzyme preferably ranges from about 0.1 IU/mg of protein to about 30,000 IU/mg of protein, where an IU is an International Unit of enzyme activity and corresponds to the conversion of 1 micromole of substrate per minute at a specified temperature. The enzyme need not be soluble in the reaction mixture, and may be attached to a solid material (supported). The specific activity of the immobilized enzyme is preferably about 0.1 IU/g immobilized enzyme to about 2000 IU/g immobilized enzyme, more preferably about 10 IU/g immobilized enzyme to about 500 IU/g of immobilized enzyme. As used herein, one unit (IU) of specific activity is equivalent to production of 1 μmol/min of cyclic poly(hexamethylene adipamide) from hexamethylenediamine and dimethyl adipate under suitable reaction conditions (e.g. 70° C.). The enzyme may be recycled and reused in the process (for example by filtering off the enzyme from the product mixture), assuming it has retained activity for catalyzing the desired reaction(s).

As used herein, the term "aprotic solvent" means an organic solvent whose molecules do not have a hydrogen atom attached to an atom of a strongly electronegative element (i.e. oxygen). As such, aprotic solvents are organic solvents that do not exchange protons with a substance dissolved in it (i.e. lacks an acidic hydrogen atom). In one embodiment, the "aprotic solvent" may optionally include a molar excess of the diester or the diamine in the reaction mixture.

As used herein, the term "recovering" means isolating, purifying, or transferring the product formed by the present process. Methods to isolate and purify the products (i.e. cyclic amide oligomers) from the reaction mixture are well known in the art may include, but are not limited to selective precipitation, filtration, solvent extraction, crystallization, and column chromatography. In one embodiment, the term "recovering" also includes transferring the product mixture (typically after filtering our the enzyme catalyst) to another reaction to create one or more additional products The term "molecular sieves" refers to crystalline metal aluminosilicates having a three-dimensional interconnecting network of silica and alumina tetrahedra. The material is comprised of uniform cavities that selectively adsorb molecules of a specific size. Molecular sieves are commercially available in a variety of pore sizes. Molecular sieves 3A (referring to a 3-angstrom pore size) and 4A (referring to a 4 angstrom pore size) are commonly used to adsorb (remove) small molecules. 3A molecular sieves are commonly used to remove water, and 4A molecular sieves are commonly used to remove water and/or methanol from polar and non-polar non-aqueous media.

As used herein, "fiber" means any material with slender, elongated structure such as polymer or natural fibers. The material can be fiberglass, ceramic fibers, carbon fibers or organic polymers such as polyester or polyamide fibers.

As used herein, a fiber "tow" or "strand" is a group of fibers together, or a bundle of fibers, which are usually wound onto spools and may or may not be twisted.

As used herein, the term "fiber preform" means an assembly of fiber tows and/or fabric held together in a desired shape.

As used herein, the term "prepreg" means a fiber material such as carbon fiber, glass fiber, or other fiber that has been impregnated with a resin material in sufficient volume as to provide the matrix of the composite, and such that the ratio of fiber to resin is closely controlled. The fiber configuration can be in tow form, woven or knitted into a fabric, or in a unidirectional tape.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

Suitable Reaction Conditions

The enzymatic methods described herein are run at temperatures at which the enzymes are active as catalysts for the desired reactions. The upper temperature limit is typically that at which the enzyme ceases to be an active catalyst. Oftentimes this is the temperature at which the enzyme is denatured in the reaction medium. This upper temperature limit will vary with the enzyme used and the process ingredients, especially the preselected solvent, used. Typically these temperatures may range from about −20° C. to about 130° C. (the upper temperature limit suitable for specialty enzymes, such as enzymes isolated from thermophillic microorganisms). In another embodiment, the temperature range is 0° to 130° C. Higher temperatures (but below the temperature at which the enzyme ceases to be active) are usually preferred because reaction(s) are often faster and solubilities of the various process ingredients are usually higher at higher temperatures. In one embodiment, useful temperatures may range from about 20° C. to about 90° C. In another embodiment, preferred temperatures may range from about 40° C. to about 75° C.

The enzymatic processes described herein are performed using enzyme catalysts that have activity pH ranges where the enzymes are active as catalysts for the desired reactions and where the pH will not significantly affect formation of the desired product. When the enzyme catalysts are used in non-aqueous reaction mixtures of the present invention, pH adjustment or control of the reaction mixture may be problematic. Zaks et al., (*J. Biol. Chem*, 263:3194-3201 (1988); *Proc. Natl. Acad. Sci. U.S.A.* 82:3192-3196 (1985)) have previously described the technique of adjusting the pH of a solution containing an enzyme catalyst to a pH that affords maximum activity of the enzyme, then recovering the enzyme catalyst from this solution (e.g., by lyophilization, precipitation, crystallization) prior to its use in a non-aqueous reaction mixture. In the present invention, the enzyme catalyst(s) may be pre-treated as described above prior to use in the present reaction mixtures.

In one embodiment, the pH range is typically from about 2 to about 10, preferably from about 3 to about 10, and most preferably from about 6 to about 8. One skilled in the art can adjust the pH of the reaction for optimal production of the present products.

The present enzymatic process may be practiced with or without the addition of an aprotic organic solvent, however the use of an aprotic organic solvent is preferred. Lipases have been shown to function in organic solvents (D. A. Cowan and A. R. Plant, *ACS Symposium Series* 498:86-107 (1992); Laane et al., *Biotechnol. Bioeng.* 30:81-87 (1987)) or in solvent free systems (U.S. Pat. No. 6,677,427; WO 94/12652).

The aprotic solvent may be polar or non-polar. Suitable examples of aprotic solvents include, but are not limited to o-dichlorobenzene, diphenyl ether, chlorobenzene, methyl-tert-butyl ether (MTBE), diisopropyl ether, tetrahydrofuran (THF), acetone, acetonitrile, 1,4-dioxane, N,N-dimethylformamide (DMF), dimethyl sulfoxide (DMSO), 1,1,1-trichloroethane, dichloroethane, toluene, xylenes, cyclohexane, heptane, isooctane, perchloroethylene, hexane, benzene, diethyl ether, ethyl acetate, methylene chloride, a molar excess of the diester, a molar excess of the diamine, and mixtures thereof. In one embodiment, either the diester or the diamine used in the reaction may be added in stoichiometric excess and serve as solvent for the reaction. In another embodiment, the aprotic solvent is selected from the group consisting of toluene, diphenyl ether, and methyl-tert-butyl ether.

Intramolecular reactions are generally favored under more dilute reaction conditions. As such, the amount of solvent used in the reaction mixture may be varied to optimize the production of cyclic amide oligomers. In one embodiment, the amount of solvent used in the reaction limits the concentration of either the diester and/or diamine reactants to less than about 2.5 molar, preferably less than about 1.5 molar, more preferably less than about 1 molar, even more preferably less than about 0.75 molar, and most preferably about 0.5 molar or less. In another embodiment, either the diester or the diamine may be added in excess and serve as the solvent in the reaction so that corresponding limited substrate (i.e. the diester or diamine substrate not added in excess) is less than about 2.5 molar, preferably less than 1.5 molar, more preferably less than about 1 molar, even more preferably less than about 0.75 molar, and most preferably about 0.5 molar or less.

The present process to produce cyclic amide oligomers may or may not include a method to remove excess water and/or small alkyl alcohols such as methanol and ethanol from the reaction mixture. However, Zaks et al., (*J. Biol. Chem*, 263:8017-8021 (1988)) have reported that there is an optimal water concentration in an enzyme-catalyzed reaction performed in an organic solvent that maximizes the enzyme activity. In one embodiment, a minimal amount of water or small alkyl alcohol may be optionally added to the enzyme-catalyzed reaction so long as the addition of the water and/or small alkyl alcohol does not adversely affect cyclic amide oligomer formation.

Yan et al., (*Biotechnol. Bioeng.* 78:31-34 (2002), and references therein) have described the use of activated molecular sieves, microwave heating, inorganic salts, evaporation, or azeotropic distillation as methods for the removal of reaction byproducts such as water, methanol and ethanol from enzyme-catalyzed reaction mixtures. On a commercial scale, control of water concentration is most easily and economically performed by evaporation or distillation, or by controlling the humidity of the gaseous atmosphere in the reaction vessel. In the Examples of the present invention, control of water concentration and removal of methanol or ethanol from the reaction mixture was most conveniently performed by inclusion of molecular sieves in the reaction mixture. Particularly preferred is the use of molecular sieves having a 3 or 4 angstrom (A) pore size. The amount of molecular sieves used in the present method may range from about 0 weight percent (wt %) to about 50 wt %, preferably about 0.1 wt % to about 30 wt %, most preferably about 5 wt % to about 20 wt % based on the total weight of the reaction mixture.

When the processes of the present invention are performed in the presence of added aprotic organic solvent, the reactants (diester and diamine) may be completely dissolved in the solution, or may be present in the reaction mixture as both dissolved and undissolved solids or liquids, such that as the reaction progresses the undissolved solids or liquids continue to dissolve and be converted to the desired products. Where the reactants are present in solution, the concentration of the reactants (diester and diamine) may range from 0.001 M to the solubility limit of each in the chosen solvent at the specified reaction temperature. In one embodiment the concentration of the diester and/or diamine in the reaction does not exceed about 2.5 molar, preferably less than about 1.5 molar, and most preferably about 0.5 molar of less. Preferably, the substrates have solubilities in the pre-selected solvent at the predetermined reaction temperature of at least 1.0 w/v percent in the solvent. More preferably the solubility is at least about 3 w/v percent, more preferably at least about 5 w/v percent. It is preferred that all of the process components (except for the enzyme catalyst) are totally soluble in the selected solvent at the predetermined reaction temperature throughout the enzyme catalyzed process. However, at the end of the process (after separation of the enzyme catalyst) the temperature of the process mixture may be lowered to preferentially precipitate and separate (as by filtration) the cyclic amide oligomers from linear amide oligomers. Optionally, the cyclic amide oligomers may precipitate in the chosen reaction solvent during the reaction process. The precipitated cyclic oligomers may be recovered by filtration or may be redissolved using a different solvent and/or an increase in solvent temperature. Preferably, a solvent and/or solvent temperature is chosen that facilitates selective precipitation of either the cyclic amide oligomers or the linear amide oligomers. Optionally, soluble cyclic amide oligomers may be separated from soluble linear amide oligomers by methods known to those skilled in the art including, but not limited to such methods as selective extraction of the cyclic or linear amide oligomer, or separation by column chromatography.

The process may be run as a batch, semi-batch, or continuous process. If volatile byproducts are removed using a flow of an inert gas (i.e., sparging), the volatiles in the gas may be recovered i.e., by cooling the gas and condensing the volatiles), and/or the gas may be recycled in the process.

Suitable Diesters and Diamines

The enzymatic process for the production of macrocyclic amide oligomers of the present invention is generally represented by the following formula:

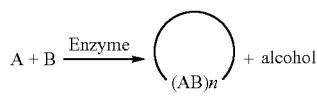

wherein n=1 to 20, preferably n=1 to 10, more preferably n=1 to 5, and most preferably n=1 to 3; A is derived from a diester, and B is derived from a diamine.

The cyclic amide oligomers can be described as cyclic unimers (wherein n=1), dimers (n=2), trimers (n=3), tetramers (n=4), and pentamers (n=5) wherein a similar naming convention can be used for cyclic amide oligomers having higher degrees of polymerization.

Cyclic amide oligomers synthesized by the present are produced in amounts of at least about 1 mole percent, preferably at least about 5 mole percent, more preferably at least 25 mole percent, and most preferably at least 50 mole percent.

The molar ratio of the diester to the diamine may be approximately equal or run under conditions of stoichiometric imbalance. The molar ratio of the diester to the diamine (diester/diamine) may range from about 0.10 to about 10. In another embodiment, the molar ratio of the diester to the diamine may range from about 0.25 to about 4. In a further embodiment, the molar ratio of the diester to the diamine may range from about 0.95 to about 1.05. In yet a further embodiment, the stoichiometric imbalance may be significantly larger when using either the diester or diamine as a solvent, resulting in a molar ratio of the diester to diamine less than 0.10 to greater than 10. As used herein, a "molar excess" will refer to a reaction condition where there is a stoichiometric imbalance between the diester and diamine in the reactive mixture. In one embodiment, the diester in the reaction mixture may be in molar excess relative to the diamine. In another embodiment, the diamine in the reaction mixture may be in molar excess relative to the diester. In a further embodiment, a molar excess of the diester or diamine functions as a solvent in the reaction mixture. In yet another embodiment, the reaction mixture comprises a molar excess of the diamine or diester and an aprotic organic solvent.

Suitable diesters have the following formula:

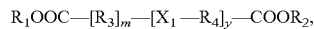

wherein $R_1$ and $R_2$ are independently a C1 to C20 hydrocarbyl group selected from one of alkyl, alkylene, aryl, haloaryl, aralkyl, aralkylene, arylene, alkoxyalkyl, and alkenyl, optionally substituted with one or more ether linkages; R3 and R4 are independently C1 to C10 hydrocarbyl group selected from one of alkyl, alkylene, aryl, haloaryl, aralkyl, aralkylene, arylene, and alkenyl; $X_1$ is selected from one or none of heteroatom or non-heteroatom, wherein the heteroatom comprises oxygen, and wherein the non-heteroatom comprises NH; y is 0 to 5; and m=0 or 1, wherein m is 1 when $X_1$ is a heteroatom or non-heteroatom.

Suitable diamines have the following formula:

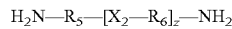

wherein $R_5$ and $R_6$ are C1 to C6 hydrocarbyl group selected from the group consisting of alkyl, akylene, aryl, haloaryl, aralkyl, aralkylene, alkarylene, arylene, and alkenyl; $X_2$ is selected from one or none of heteroatom or non-heteroatom, wherein the heteroatom comprises oxygen or sulfur, and wherein the non-heteroatom comprises amine, carbonyl, or C1 to C6 hydrocarbyl group selected from one of alkyl, alkylene, aryl, haloalkyl, aralkyl, aralkylene, arylene or alkenyl; z is from 0 to 20; and wherein $R_5$ and $R_6$ may be the same or different.

In one embodiment, $R_1$ and $R_2$ are independently a C1 to C6 hydrocarbyl group optionally substituted with one or more ether linkages; m is 0 or 1; $R_3$ is C1 to C10 hydrocarbyl group; y is 0 to 5; $R_4$ is a C1 to C3 hydrocarbyl group; $R_5$ and R6 are independently C1 to C6 hydrocarbyl group; z is 0 to 5; and $X_2$ is one or none of heteroatom or non-heteroatom, wherein the heteroatom comprises oxygen or sulfur, and wherein the non-heteroatom comprises amine, carbonyl, or C1 to 4 hydrocarbyl group.

In another embodiment, $R_1$ and $R_2$ are independently a C1 to C6 alkyl group optionally substituted with one or more ether linkages; m is 1; $R_3$ is C1 to C10 alkyl group; y is 0; $R_5$ and $R_6$ are independently is C1 to C6 hydrocarbyl group; z is 0 to 4; and $X_2$ is one or none of heteroatom or non-heteroatom, wherein the heteroatom comprises oxygen or sulfur, and wherein the non-heteroatom comprises amine, carbonyl, or C1 to 4 hydrocarbyl group.

In a further embodiment, $R_1$ and $R_2$ are independently a C1 to C6 alkyl group optionally substituted with an ether linkage; m is 1; $R_3$ is C1 to C10 alkyl group; y is 0; $R_5$ is C1 to C6 hydrocarbyl group; z is 0 to 4; $R_6$ is a C1 to C4 alkyl group; $X_2$ is one or none of heteroatom or non-heteroatom, wherein the heteroatom is oxygen, and wherein the non-heteroatom is amine or C1 to C4 alkyl group.

In yet another embodiment, $R_1$ and $R_2$ are independently a C1 to C2 alkyl group; m is 1; $R_3$ is C1 to $C_{10}$ alkyl group; y is 0; $R_5$ is C1 to C6 alkyl group; z is 1; $R_6$ is a C1 to C4 alkyl group; and $X_2$ is C1 to C2 alkyl group.

Suitable diesters include, but are not limited to dialkyl adipate, dialkyl malonate, dialkyl succinate, dialkyl glutarate, dialkyl phthalate, dialkyl isophthalate, dialkyl terephthalate, dialkyl maleate, dialkyl fumarate, dialkyl oxalate, dialkyl phenylmalonate, dialkyl suberate, dialkyl sebacate, bis(2-butoxyethyl)adipate, dimethyl 2,2'-oxybisacetate, dimethyl 3,3'-oxybispropanoate, dimethyl 3,3'-[1,2-ethanediylbis(oxy)]bispropanoate, and β-alanine, N-(3-methoxy-3-oxopropyl) methyl ester, and mixtures thereof. In one particular embodiment, the diester is dialkyl adipate.

Suitable diamines include, but are not limited to 1,6-diaminohexane (hexamethylene diamine), 1,12-diamino dodecane, 1,10-diaminodecane, diethylenetriamine, triethyleneglycol diamine, ethylenediamine, propylenediamine, triethylenetetramine, dipropylenetriamine, tripropylenetetramine, tetrapropylenepentamine, spermine, bis-(hexamethylenetriamine), o-phenylenediamine, poly(oxyethylene)diamine, poly(oxypropylene)diamine, polyetherdiamine, and mixtures thereof. In one particular embodiment, the diamine is 1,6-diaminohexane, 1,10-diamino dodecane or 1,12-diamino dodecane.

Cyclic amide oligomers produced by the present invention include, but are not limited to cyclic poly(ethylene oxalamide), poly(hexamethylene oxalamide), cyclic poly(decamethylene oxalamide), cyclic poly(dodecamethylene oxalamide), cyclic poly(ethylene fumaramide), cyclic poly(hexamethylene fumaramide), cyclic poly(decamethylene fumaramide), cyclic poly(dodecamethylene fumaramide), cyclic poly(propylene malonamide), cyclic poly(hexamethylene malonamide), cyclic poly(decamethylene malonamide), cyclic poly(dodecamethylene malonamide), cyclic poly(ethylene maleiamide), cyclic poly(hexamethylene maleiamide), cyclic poly(decamethylene maleiamide), cyclic poly(dodecamethylene maleiamide), cyclic poly(hexamethylene succinamide), cyclic poly(decamethylene succinamide), cyclic poly(dodecamethylene succinamide), cyclic poly(hexamethylene glutaramide), cyclic poly(decamethylene glutaramide), cyclic poly(dodecamethylene glutaramide), cyclic poly(ethylene adipamide), cyclic poly(tetramethylene adipamide), cyclic poly(pentamethylene adipamide), cyclic poly(hexamethylene adipamide), cyclic poly(decamethylene adipamide), cyclic poly(dodecamethylene adipamide), cyclic poly(trimethylhexamethylene adipamide), cyclic poly(o-phenylene adipamide), cyclic poly(ethylene pimelamide), cyclic poly(hexamethylene pimelamide), cyclic poly(decamethylene pimelamide), cyclic poly(dodecamethylene pimelamide), cyclic poly(propylene suberamide), cyclic poly(hexamethylene suberamide), cyclic poly(decamethylene suberamide), cyclic poly(dodecamethylene suberamide), cyclic poly(ethylene azelamide), cyclic poly(hexamethylene azelamide), cyclic poly(decamethylene azelamide), cyclic poly(dodecamethylene azelamide), cyclic poly(ethylene sebacamide), cyclic poly(hexamethylene sebacamide), cyclic poly(decamethylene sebacamide), cyclic poly(dodecamethylene sebacamide), cyclic poly(triethyleneglycol sebacamide), cyclic poly(bis-hexamethyleneamine sebacamide), cyclic poly(o-phenylene sebacamide), cyclic poly(bis-cyclohexylmethane sebacamide), cyclic poly(ethylene dodecanediamide), cyclic poly(hexamethylene dodecanediamide), cyclic poly(decamethylene dodecanediamide), cyclic poly(dodecamethylene dodecanediamide), cyclic poly(triethyleneglycol dodecanediamide), cyclic poly(bis-hexamethyleneamine dodecanediamide), cyclic poly(bis-cyclohexylmethane dodecanediamide), cyclic poly(o-phenylene dodecanediamide), cyclic poly(p-phenylene terephthalamide), cyclic poly(m-phenylene terephthalamide), cyclic poly(o-phenylene terephthalamide), cyclic poly(p-phenylene isophthalamide), cyclic poly(m-phenylene isophthalamide), cyclic poly(o-phenylene isophthalamide), cyclic poly(p-phenylene phthalamide), cyclic poly(m-phenylene phthalamide), cyclic poly(o-phenylene phthalamide), cyclic poly(bis-cyclohexylmethane terephthalamide), cyclic poly(bis-cyclohexylmethane terephthalamide), cyclic poly(bis-cyclohexylemethane terephthalamide), cyclic poly(trimethylhexamethylene terephthalamide), cyclic poly(trimethyl hexamethylene isophthalamide), cyclic poly(trimethylhexamethylene phthalamide), cyclic poly(hexamethylene terephthalamide), cyclic poly(decamethylene terephthalamide), cyclic poly(dodecamethylene terephthalamide), cyclic poly(triethyleneglycol terephthalamide), cyclic poly(bis-hexamethyleneamine terephthalamide), cyclic poly(hexamethylene phthalamide), cyclic poly(decamethylene phthalamide), cyclic poly(dodecamethylene phthalamide), cyclic poly(triethyleneglycol phthalamide), cyclic poly(bis-hexamethyleneamine phthalamide), cyclic poly(hexamethylene isophthalamide), cyclic poly(decamethylene isophthalamide), cyclic poly(dodecamethylene isophthalamide), cyclic poly(triethyleneglycol isophthalamide), or cyclic poly(bis-hexamethylene amine isophthalamide).

In a preferred embodiment, cyclic amide oligomers include, but not limited to cyclic poly(ethylene oxalamide), cyclic poly(propylene malonamide), cyclic poly(tetramethylene adipamide), cyclic poly(hexamethylene adipamide), cyclic poly(decamethylene adipamide), cyclic poly(dodecamethylene adipamide), cyclic poly(hexamethylene suberamide), cyclic poly(dodecamethylene suberamide), cyclic poly(hexamethylene azelamide), cyclic poly(ethylene sebacamide), cyclic poly(decamethylene sebacamide), cyclic poly(dodecamethylene sebacamide), cyclic poly(triethyleneglycol sebacamide), cyclic poly(bis-hexamethylene sebacamide), cyclic poly(ortho-phenylene sebacamide), cyclic poly(hexamethylene dodecanediamide), cyclic poly(decamethylene dodecanediamide), or cyclic poly(dodecamethylene dodecanediamide).

In a particularly preferred embodiment, the cyclic amide oligomers are cyclic poly(hexamethylene adipamide) and cyclic poly(dodecamethylene adipamide).

Use of Non-cyclic Oligomers to Produce Cyclic Amide Oligomers

In another aspect, non-cyclic oligomers may be used as a substrate for the enzymatic production of cyclic amide oligomers. The non-cyclic oligomers can include linear oligomers, branched oligomers, mixtures of non-cyclic oligomers, or mixtures of non-cyclic oligomers with diesters and/or diamines. For example, a linear oligomer derived from the polymerization of a diester (A) with a diamine (B)→(A-B)$_n$ could be used to produce cyclic amide oligomers as long as the resulting linear oligomer was comprised of at least one ester and at least one amine group and wherein n is 1 or more, preferably 1 to about 30, more preferably 1 to about 20, more preferably 1 to about 10, and even more preferably 1 to 5.

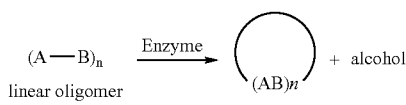

Intramolecular reactions are typically favored when using dilute reaction conditions. Enzymatic conversion of linear amide oligomers to cyclic amide oligomers is preferably conducted in an aprotic organic solvent.

Depending upon the average length of the linear amide oligomer, the solubility limit will vary. For shorter linear amide oliogimers (for example, n=5 or less), the amount of solvent used in the enzymatic conversion of linear amide oligomers (LAOs) to cyclic amide oligomers (CAOs) may be adjusted so that the concentration of LAOs in the reaction is generally less than about 2.5 molar, preferably less than about 1 molar, more preferably less than about 0.75 molar, and even more preferably less than 0.1M, and most preferably no more than about 0.01 molar. For longer linear amide oligomers (for example, n>5), the amount of solvent used may be adjusted so that the concentration of the linear amide oligomer is near the saturation concentration of the linear amide oligomer, preferably about 0.3 molar or less, more preferably about 0.1 molar or less.

Suitable reaction conditions (the pH, aprotic solvent(s) used, temperature, and hydrolytic enzyme catalyst) for the enzymatic conversion of linear amide oligomers to cyclic amide oligomers are those described previously (see "Suitable Reaction Conditions").

Isolation and Analysis of the Cyclic Amide Oligomers

The desired cyclic amide oligomers (CAOs) may be recovered by purification/isolation techniques known in the art. For example, if the CAO is a solid it may be recovered from solution by cooling the solution and/or removing some or all of the solvent, and recovering the solid CAO, for example by filtration. If there is some linear polyamide (of any molecular weight) remaining in the process it may be possible to separate the CAOs from the linear polyamides by differential precipitation or extraction from one or more solvents. Examples of suitable solvents include, but are not limited to, dichloromethane, chloroform, dimethylacetamide, hexafluorisopropanol, acetone, and xylene. Other methods for separation of cyclic oligomers from linear chains include, but are not limited to, chromatography, crystallization (for example, to separate Nylon 6,6 cyclics) and sublimation (for example, to separate Nylon 12,6 cyclics).

There are many tools available for polymer analysis including, but not limited to thin layer chromatography, size exclusion chromatography, NMR spectroscopy (both proton and carbon), infrared (IR) spectroscopy, high performance liquid chromatography (HPLC), gas chromatography, and mass spectroscopy (including MALDI-TOF MS and ESI-MS) (Klun et al., *Polymer,* 42:7095-7099 (2001)).

Manufacture of Shaped Products using Cyclic Amide Oligomers

In one aspect of the invention, shaped articles can be produced using a cyclic amide oligomer material (with or without fillers) by polymerizing it in the process of forming the article, using processes such as, but not limited to, injection and rotational molding, resin film infusion, resin transfer molding, filament winding, powder coating to create a prepreg or film, hot melt prepreg preparation, compression molding, roll wrapping, and pultrusion with or in some cases without reinforcement. The only proviso is that conditions allow for the polymerization of the cyclic amide oligomer to form high molecular weight polyamide; that is, the cyclic amide oligomer should be heated at least to its melting point. Generally, most of such processes require that the resin to be processed have a low melt viscosity; therefore, cyclic amide oligomers (which have low melt viscosity) are particularly suitable for such processing.

For example, a molding process for manufacturing articles from cyclic amide oligomer includes placing in a mold at least one cyclic amide oligomer and a mixture or adduct of at least one polymerization catalyst and heating the contents of the mold to a temperature high enough for polymerization of the oligomer to take place. This is above the melting point of the oligomer, typically in the range of about 120 to about 280° C. Molten oligomer and catalyst can be injected into the mold at much lower pressure than the 5,000 to 20,000 psi (34 MPa to 64 MPa) typical of injection molding processes because of the low viscosity of the molten oligomer.

In compression molding, the oligomer(s) and catalyst(s) are placed between a top die and a lower die within a press. The oligomer(s) and catalyst(s) are typically loaded onto a fibrous base material. The dies of the mold are pressed together with enough pressure to evenly fill the mold, and the mold contents are heated to a high enough temperature for polymerization to take place. Compression molding is used for making plastic composite parts that are thin and generally flat with mild features and contours such as truck and auto body panels, bumper beams, various trays and machine housings.

In rotational molding, the molding process additionally comprises rotating the mold about two axes simultaneously, so that the contents roll over the intended areas of the inside of the mold, beginning the rotation before the contents are heated, and continuing to rotate the mold until the content polymerizes and solidifies. Rotational molding is a process for making hollow thermoplastic articles, such as a wide variety of fluid storage tanks, tractor fenders and large children's toys.

In resin film infusion, a layer or film of the cyclic amide oligomer (s) containing the catalyst(s) is placed in the mold adjacent to a dry layer of fibrous material, and, when the contents of the mold are heated, the oligomer(s) and catalyst(s) are forced to infuse into the dry layer of fibrous material. Resin film infusion is a process for making plastic composite articles that are predominantly flat on one face and may have detailed features. An illustrative example of such articles is aircraft wing skins which are typically constructed of a composite made with carbon fiber and epoxy resin.

Reaction Injection Molding (RIM) has traditionally been used with urethane based chemistries, but efforts by DSM and Dupont focused on the application of RIM technology to caprolactam (Macosko, C., *Fundamentals of Reaction Injection Molding,* Hanser Publishers: New York, N.Y.; Chapter 7. (1989)). The application of RIM technology to caprolactam developed from early efforts that focused on casting technology. For example, Darnell et al. (U.S. Pat. No. 3,309,343) examined the efficacy of activated monomer approaches for the caprolactam chain growth polymerization. Typically, interest in ring opening polymerization (ROP) of cyclic amides was due to the low melt viscosity of the cyclic amide monomer and its transformation into a high molecular weight polyamide in the RIM like process (Brunelle, D. J., "Synthesis and Polymerization of Cyclic Polyester Oligomers" in *Modern Polyesters*, Schiers, J. and Long, T. E., Eds, Wiley and Sons, New York, N.Y. (2003)). The inherently low melt viscosity state (<30 cps) of the monomer renders the macrocyclic approach useful for the development of small intricate parts, excellent wetting of fiber mats, and void free materials. In addition, the absence of end-groups from the cyclic monomers facilitates the preparation of unusually high molecular weight polymers. These cyclic monomers are readily applicable to a broad range of polymer processing techniques, such as pultrusion, resin transfer molding, and casting. For example cyclic poly(hexamethylene adipamide) is useful for fiber, films and for moldings such as electrical and automotive parts.

The compositions and methods of the invention may be used to manufacture articles of various size and shape from various cyclic amide oligomers. Exemplary articles that may be manufactured by the invention include without limitation automotive body panels and chassis components, bumper beams, aircraft wing skins, windmill blades, fluid storage tanks, tractor fenders, tennis rackets, golf shafts, windsurfing masts, toys, rods, tubes, bars stock, bicycle forks, and machine housings.

In the manufacture of an article, one or more of various types of fillers may be included. A particular filler often is included to achieve a desired purpose or property, and may be present in the resulting polyamide polymer. For example, the purpose of the filler may be to increase the strength of the polyamide polymer product. Boron nitride is used as a filler in applications that require high levels of heat conductivity and low levels of electrical conductivity. A filler also may provide or provide weight or bulk to achieve a particular density, be a substitute for a more expensive material, and/or provide other desirable properties as recognized by a skilled artisan. Illustrative examples of fillers are, among others, fumed silica, titanium dioxide, calcium carbonate, chopped fibers, fly ash, glass microspheres, micro-balloons, crushed stone, nanoclay, linear polymers, and monomers. A filler may be added before, during, or after the polymerization reaction. The filler is added generally between about 0.1% and 70% by weight of the total (i.e., oligomer plus catalyst plus filler plus any other additives that may be present), depending on the filler and the purpose for adding the filler. For example, the percentage is preferably between 25% and 50% by weight in the case of calcium carbonate, between 2% and 5% by weight in the case of nanoclays, and between 25% and 70% by weight in the case of glass microspheres. Fillers can be used to prepare polyamide polymer composites.

Furthermore, in the manufacture of an article, additional components (e.g., additives) may be added. Illustrative additives include colorants, pigments, magnetic materials, antioxidants, UV stabilizers, plasticizers, flame retardants, lubricants, and mold releases.

Cyclic amide oligomers created by the present invention typically can be used in essentially any application that uses linear amide oligomers. Additional uses of cyclic amide oligomers include, but are not limited applications such as powder coatings (U.S. Pat. No. 6,141,103 and U.S. Pat. No. 6,376,026), creping adhesives, and wet strength resins to make cellulose products (U.S. Pat. No. 6,677,427).

In one embodiment, the amount of cyclic amide oligomer used in a process to form a shaped article is at least 1 wt % of the starting material used in the article forming process, preferably at least 5 wt %, more preferably at least 25 wt %, even more preferably at least 50 wt %, yet even more preferably at least 90 wt %, and most preferably at least 99 wt %

Applicants specifically incorporate the entire contents of all cited references in this disclosure. Further, when an amount, concentration, or other value or parameter is given either as a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

All reagents were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified. The hydrolytic enzymes were obtained from BioCatalytics Inc. (Pasadena, Calif.), Boehringer Mannheim GmbH (Mannheim, Germany), Roche Diagnostics (Indianapolis, Ind.), Amano Enzymes, Inc. USA (Elgin, Ill.), or Novozymes A/S (Bagsvaerd, Denmark).

The meaning of abbreviations is as follows: "h" means hour(s), "min" means minute(s), "mL" means milliliters, "μL" mean microliters, "L" means liters, "mg" means milligrams, "MPA" means macrocyclic polyamide, "CAO" means cyclic amide oligomer, "HMD" means hexamethylene diamine, "DMA" means dimethyl adipate, "DADD" means diamino dodecane, "DPE" means diphenyl ether, "MTBE" means methyl-tert-butyl ether, "o-PD" means ortho-phenyl diamine, "MC %" means percent monomer (diester) conversion, "cU %" means molar percent cyclic unimer formed, "cD %" means molar percent cyclic dimer formed, "cT %" means molar percent cyclic trimer formed, "CAO %" means molar percent of total cyclic amide oligomer formed, "wt %" means weight percent, "M" means molarity, "MALDI-TOF MS" means matrix assisted laser desorption/ionization time-of-flight mass spectroscopy, "HPLC MS" means high performance liquid chromatography with mass spectroscopy, and "rpm" means revolutions per minute.

General Methods

HPLC Determination of Diester Conversion

A Waters Alliance 2695 separation module equipped with 2487 UV detector (210 nm), and a Novapak C18 column (3.9×150 mm, 60A pore size, 4 μm particle size) was used. The water:acetonitrile mobile phase was run at 1 mL/min with the following gradient:

| Time (min) | Water (%) | Acetonitrile (%) |
|---|---|---|
| 0 | 90 | 10 |
| 20 | 30 | 70 |
| 25 | 0 | 100 |
| 28 | 0 | 100 |
| 30 | 90 | 10 |
| 35 | 90 | 10 |

The appropriate diester or reaction sample without solvent was dissolved in acetonitrile/water. The following diester retention times were observed: dimethyl oxalate (C2) 2.36 min, dimethyl malonate (C3) 3.05 min, dimethyl succinate (C4) 4.05 min, dimethyl adipate (C6) 7.7 min, dimethyl suberate (C8) 12.3 min, dimethyl sebacate (C10) 16.5 min, diethyl adipate 12 min, bis(2-butoxyethyl) adipate 19.4 min. Monomer conversion was determined by comparison of the diester peak area in the reaction mixture with a calibration curve generated with known concentrations of the diester.

MALDI-TOF Analysis of the Oligomeric Compositions

Product mixtures were dissolved in a toluene/methanol mixture (50/50 or 20/80 as specified in examples) to make an approximately 0.2 M solution (or solution of at least 0.01M for highly diluted reactions at 0.025M of reactants). These samples were diluted 300:1 (or 15:1 for highly diluted reaction mixture samples) in hexafluoroisopropanol (HFIP). Samples that did not appear to be soluble in toluene/methanol were dissolved instead in trichloroethanol (TCE) and diluted 300:1 (or 15:1 for highly diluted reaction mixture samples) with TCE. Solutions were deposited onto a matrix assisted laser desorption/ionization (MALDI) target plate in the following manner. First, a saturated solution of 2,5-dihydroxybenzoic acid (DHB) (0.5 mL) in acetone was added to the target plate to act as matrix. Then, 0.5 mL of either the HFIP or the TCE reaction mixture solution was added to the dried matrix spot. The HFIP solutions dried rapidly in air and the TCE solutions were dried under vacuum. MALDI-TOF mass spectra were obtained on all samples using a PerSeptives Biosystems Voyager-DE STR MALDI-TOF mass spectrometer) operated using a nitrogen (337 nm) laser. Each mass spectrum is an accumulation of between 100 and 250 laser events.

Cyclic species and linear chains with ester-amine, ester-ester, amine-amine, acid-amine, acid-ester, and acid-acid terminals were observed in mass spectra as $H^+$, $Na^+$, or $K^+$ adducts. For example, cyclic nylon 12,6 unimer, $[NH(CH_2)_{12}NH-C(O)(CH_2)_6C(O)]_1$, was detected at 311, 333, and/or 349 Da as hydrogen, sodium, and potassium-cationized ions, respectively.

Relative molar percent of cyclic species among all the oligomers was calculated from areas of all the observed ions for the corresponding oligomers. Validity of this quantitation, namely similar ionization efficiency for low molecular weight oligoamides (oligoamides observed in the reactions that did not exceed 2500 Da and were most abundant below 1000 Da) was evaluated as follows. Low molecular weight nylon 6,6 oligomers in which the trimer was the most abundant species were synthesized in a manner that the dominant oligomers were linear with acid ends. Likewise, similar linear oligomers were synthesized with dominant amine ends and also with dominant acid-amine ends. Cyclic oligomers with the trimer as the most abundant species were obtained by a methanol extraction of nylon 6,6. Each of the solid materials was weighed and dissolved in HFIP to make approximately equimolar solutions. Identical conditions were used in separately depositing the solutions onto a MALDI-TOF target using DHB as matrix and in obtaining the mass spectra. The contamination of oligomers other than the dominant oligomer was examined for each spectra. The four solutions were then mixed to make an equimolar mixture of low-mass nylon 6,6 oligomers having acid ends, amine ends, acid-amine ends, and cyclics. The total ion abundances observed for each oligomer type in the MALDI-TOF mass spectrum of the equimolar mixture, factoring in the contamination in each component, showed that any discrimination in the MALDI-TOF desorption/ionization process relative to different ends or cyclics was minimal.

Example 1

Synthesis of Macrocyclic Amides from Hexamethylene Diamine (HMD) or Diaminododecane (DADD) (0.5 M) and Dimethyl Adipate (DMA) with Novozym® 435 (10 wt %) in Toluene or Diphenyl Ether (DPE)

An 8-mL reaction vial equipped with a stirring bar and containing 200 mg of Novozym® 435 (Novozymes A/S), 116 mg of HMD or 200 mg DADD, selected amounts of DMA (Table 1), 1.84 mL, 1.72 mL, or 1.23 mL of toluene or DPE for DMA/HMD molar ratios of 0.25, 1, or 4, respectively, or 1.76 mL, 1.64 mL, or 1.14 mL of toluene or DPE for DMA/DADD ratios of 0.25, 1, or 4, respectively, and 200 mg of 4A molecular sieves, was incubated at elevated temperature at constant stirring.

After appropriate time, the reactions were removed from heat, placed in polypropylene centrifuge tubes using 2 mL of warm (60° C.) toluene/methanol (80/20), centrifuged at 12000 rpm for 5 min, and the supernatant was collected. Addition of warm toluene/methanol (80/20), centrifugation, and supernatant removal were repeated, and the supernatant fractions were combined. Supernatant was analyzed by MALDI-TOF MS for cyclic amide oligomer content (CAO, %).

Cyclics other than cyclic unimer (cU, %) and cyclic dimer (cD, %) were not detected. No cyclic compounds were found in HMD reactions without enzyme, and less than 1% cyclic unimer was detected in DADD reactions without enzyme.

TABLE 1

Effects of aliphatic diamine size (C6 or C12) and diester (dimethyladipate) to diamine ratio, solvent, temperature, and reaction time on cyclic amide oligomer synthesis.

| Diamine | Diester/Diamine molar ratio | Solvent | Temp, °C. | Time, h | cU, % | cD, % | CAO, % |
|---|---|---|---|---|---|---|---|
| HMD | 0.25 | DPE | 70 | 6 | 5 | 10.2 | 15.2 |
| HMD | 0.25 | Toluene | 70 | 24 | 7 | 7 | 14 |
| HMD | 1 | Toluene | 60 | 15 | 5.3 | 1.3 | 6.6 |
| HMD | 1 | Toluene | 60 | 15 | 3.6 | 1.4 | 5 |
| HMD | 0.25 | DPE | 50 | 24 | 1.7 | 0 | 1.7 |
| HMD | 0.25 | Toluene | 50 | 6 | 1.3 | 0 | 1.3 |
| HMD | 4 | Toluene | 50 | 24 | 0.5 | 0 | 0.5 |
| DADD | 1 | Toluene | 60 | 15 | 53.4 | 1.6 | 55 |
| DADD | 1 | Toluene | 60 | 15 | 35.7 | 1.9 | 37.6 |
| DADD | 0.25 | Toluene | 50 | 24 | 21.7 | 0.5 | 22.2 |
| DADD | 0.25 | DPE | 70 | 24 | 21.3 | 0.7 | 22 |
| DADD | 0.25 | Toluene | 70 | 6 | 20.6 | 1.1 | 20.6 |
| DADD | 0.25 | DPE | 50 | 6 | 14.1 | 0 | 14.1 |
| DADD | 4 | Toluene | 70 | 24 | 15.2 | 0 | 15.2 |
| DADD | 4 | DPE | 70 | 6 | 14.8 | 0 | 14.8 |

TABLE 1-continued

Effects of aliphatic diamine size (C6 or C12) and diester (dimethyladipate) to diamine ratio, solvent, temperature, and reaction time on cyclic amide oligomer synthesis.

| Diamine | Diester/ Diamine molar ratio | Solvent | Temp, °C. | Time, h | cU, % | cD, % | CAO, % |
|---|---|---|---|---|---|---|---|
| DADD | 4 | DPE | 50 | 24 | 10.9 | 0 | 10.9 |
| DADD | 4 | Toluene | 50 | 6 | 7.7 | 0 | 7.7 |

Example 2

Synthesis of Macrocyclic Amides from HMD or DADD (0.5M) and DMA (0.5M) with Novozym® 435 (10 wt %) in Toluene at 70° C.

An 8-mL reaction vial equipped with a stirring bar and containing 200 mg of Novozym® 435, 116 mg of HMD or 200 mg DADD, 164 µL DMA, 1.72 mL (for HMD) or 1.64 mL (for DADD) toluene, and a selected amount (Table 2) of 4A or 3A molecular sieves (Aldrich), was incubated at 70° C. with constant stirring.

After 24 h the reactions were removed from heat, placed in propylene centrifuge tubes using 2 mL of warm (60° C.) toluene/methanol (80/20), centrifuged at 12000 rpm for 5 min, and the supernatant was collected. Addition of warm toluene/methanol (1/1) (vol/vol), centrifugation, and supernatant removal were repeated, and the two supernatant fractions were combined. Supernatant and solid products dissolved in trichloroethanol were analyzed by MALDI-TOF MS for cyclic polyamide content—percent of cyclic unimer (cU, %), cyclic dimer (cD, %), and total cyclic amide oligomers (cyclics larger than dimer were not observed) (CAO, %). Monomer (diester) conversion (MC, %) was determined by HPLC analysis of the supernatant. In reactions where solid products (Solid, wt %) were formed, molar content of cyclic compounds in the overall product mixture was calculated from content of cyclics in supernatant, content of cyclics in solid products, and relative weights of supernatant and solids (Table 2). Typically, supernatant was enriched with cyclic species relative to solids. In the latter, the shorter cyclic species were physically entrapped in relatively small quantities, and the solids consisted mostly of longer linear polyamide chains (typically of still low molecular weight <2500 Da) with low solubility in toluene/methanol.

TABLE 2

Effect of Molecular Sieves Content on Macrocyclic Amide Synthesis

| Amine | Sieves*, wt % | MC, % | Solid, wt % | cU, % | cD, % | CAO, % |
|---|---|---|---|---|---|---|
| HMD | 0 | 57 | 7 | 0.05 | 0 | 0.05 |
| HMD | 10 | 93 | 35 | 1.5 | 0.4 | 1.9 |
| HMD | 10 | 93 | 29 | 2.6 | 1.3 | 3.9 |
| HMD | 20 | 86 | 30 | 4.3 | 3.1 | 7.4 |
| HMD | 50 | 89 | 41 | 3.5 | 4.5 | 8 |
| DADD | 0 | 100 | 97 | 19.6 | 0.4 | 20 |
| DADD | 10 | 95 | 11 | 35.6 | 1.4 | 37 |
| DADD | 10* | 66 | 17 | 32.6 | 0.8 | 33.4 |
| DADD | 20 | 100 | 59 | 22.5 | 1.5 | 24.1 |

*3A molecular sieves were used

Example 3

Synthesis of Macrocyclic Amides from HMD or DADD and DMA at Equimolar Ratio at Various Concentrations with Novozym® 435 (10 wt %) in Toluene at 70° C.

An 8-mL reaction vial equipped with a stirring bar and containing 200 mg of Novozym® 435, 200 mg of 4A molecular sieves, appropriate amount of HMD or DADD and DMA, and toluene to yield 2 mL of reaction solution with selected molarity (Table 3), was incubated at 70° C. at constant stirring. Reactions prepared in exactly the same way but without immobilized enzyme were performed as non-enzymatic controls.

After 24 h the reactions were removed from heat, filtered through 175 µm glass filter with warm (60° C.) toluene/methanol (1/1), and filtrate and solid products dissolved in trichloroethanol were analyzed by MALDI-TOF MS for cyclics content (percent of cyclic unimer (cU, %), cyclic dimer (cD, %), and total cyclic aminde oligomers (cyclic larger than dimer were not observed) (CAO, %). Monomer (diester) conversion (MC, %) was determined by HPLC analysis of filtrate as described in Example 2. In reactions where solid products (Solid, wt %) were formed, content of cyclic compounds in product mixture was calculated from content of cyclics in filtrate, content of cyclics in solid productys, and relative weights of filtrate and solids (Table 3).

TABLE 3

Effect of Substrate Concentration on Macrocyclic Amide Synthesis

| Amine | Amine, M DMA, M | Enzyme Catalyst, wt % | MC, % | Solid, wt % | cU, % | cD, % | cT, % | CAO, % |
|---|---|---|---|---|---|---|---|---|
| HMD | 0.025 | 0 | 0 | nd | 4.5 | 3.5 | 0 | 8 |
| HMD | 0.025 | 10 | 10 | 21 | 33.7 | 30.5 | 3.1 | 67.3 |
| HMD | 1.0 | 10 | 2 | 2 | 1.2 | 0.7 | 0 | 1.9 |
| HMD | 1.0 | 0 | 0 | 2 | 0 | 0 | 0 | 0 |
| DADD | 0.025 | 0 | 1 | nd | 0 | 0 | 0 | 0 |
| DADD | 0.025 | 10 | 100 | 38 | 67.4 | 0 | 0 | 87.4 |
| DADD | 0.25 | 10 | 100 | 28 | 16.8 | 11.7 | 0 | 28.5 |
| DADD | 0.5 | 10 | 100 | 28 | 34.8 | 3 | 0 | 37.8 |
| DADD | 1.0 | 10 | 100 | 42 | 33.7 | 0.3 | 0 | 34 |
| DADD | 1.0 | 0 | nd | nd | 0 | 0 | 0 | 0 | nd = not determined.

Example 4

Synthesis of Macrocyclic Amide from DADD (0.5M) and DMA as a Solvent with Novozym® 435 (10 wt %) at 70° C.

An 8-mL reaction vial equipped with a stirring bar and containing 200 mg of Novozym® 435, 200 mg of DADD, and 1.8 mL of DMA, was incubated at 70° C. at constant stirring for 24 hours. Reaction prepared in exactly the same way but without immobilized enzyme was performed as non-enzymatic control.

The reactions were analyzed as described in Example 3. DMA conversion was not determined. Reactions yielded 13.4% cyclic unimer (no dimer was formed) with enzyme and without molecular sieves 4A, 3.5% unimer (no dimer formed) with enzyme in the presence of 10 wt % molecular sieves 4A, and no cyclic oligomers were formed without enzyme.

Example 5

Synthesis of Macrocyclic Amide from DADD (0.25 M) and DMA (0.25 M) with Novozym® 435 (10 wt %) in Toluene at 70° C. with Added Water (0.2 M)

An 8-mL reaction vial equipped with a stirring bar and containing 200 mg of Novozym® 435 (when used), 200 mg of DADD, 164 μL of DMA, 7.2 μL water (added optionally), and 1.64 mL toluene, was incubated at 70° C. for 24 h at constant stirring. Reaction prepared in exactly the same way but without immobilized enzyme was performed as non-enzymatic control.

The reactions were analyzed as described in Example 3. Results are shown in Table 4.

TABLE 4

Effect of Addition of Water on Macrocyclic Amide Synthesis

| Enzyme Catalyst, wt % | Addition of water | MC, % | Solid, wt % | cU, % | cD, % | CAO, % |
|---|---|---|---|---|---|---|
| 10 | Yes | — | 57 | 40.8 | 3.2 | 44 |
| 10 | No | 100 | 28 | 16.8 | 11.7 | 28.5 |
| 0 | Yes | — | — | 0 | 0 | 0 |

Example 6

Synthesis of Macrocyclic Amide from DADD (0.5M) and DMA (0.5M) with Novozym® 435 at Different Enzyme Concentrations in Toluene at 70° C.

An 8-mL reaction vial equipped with a stirring bar and containing an appropriate amount of Novozym® 435, 200 mg of DADD, 164 μL of DMA, and 1.64 mL toluene, was incubated at 70° C. at constant stirring. Reaction at 0.025 M reactants prepared in exactly the same way but without immobilized enzyme was performed as non-enzymatic control.

The reactions were analyzed as described in Example 3. Results are shown in Table 5 and FIG. 1.

TABLE 5

Effect of Enzyme Catalyst Weight Percent on Macrocyclic Amide Synthesis

| Enzyme Catalyst, wt % | MC, % | Solid, wt % | cU, % | cD, % | CAO, % |
|---|---|---|---|---|---|
| 0 | 82 | 0 | 0 | 0 | 0 |
| 1 | 100 | 0 | 15.9 | 0 | 15.9 |
| 5 | 91 | 37 | 28.6 | 1.6 | 30.2 |
| 10 | 100 | 28 | 34.8 | 3 | 37.8 |
| 20 | 91 | 40 | 41.8 | 1.9 | 43.7 |

Example 7

Synthesis of Macrocyclic Amide from DADD (0.1M) and DMA (0.1M) with Novozym® 435 (10 wt %) in Toluene at Different Temperatures An 8-mL reaction vial equipped with a stirring bar and containing 200 mg of Novozym® 435, 40 mg DADD, 33 μL DMA, and 1.93 mL toluene, was incubated at 45, 70, or 90° C. for 24 h with constant stirring.

The reactions were analyzed as described in Example 3. Results are shown in Table.

TABLE 6

Temperature Effect on Cyclic Amide Oligomer Synthesis

| Temp. ° C. | Enzyme Catalyst, wt % | MC, % | Solid, wt % | cU, % | cD, % | CAO, % |
|---|---|---|---|---|---|---|
| 45 | 10 | 100 | 78 | 6.9 | 1.3 | 8.2 |
| 45 | 0 | 3 | 0 | 0 | 0 | 0 |
| 70 | 10 | 97 | 73 | 33.3 | 20.8 | 54.1 |
| 70 | 0 | 6 | 0 | 0 | 0 | 0 |
| 90 | 10 | 97 | 68 | 21 | 16.3 | 36.2 |
| 90 | 0 | 13 | 0 | 0 | 0 | 0 |

Example 8

Synthesis of Macrocyclic Amide from DADD (0.1M) and DMA (0.1M) with Various Enzymes (10 wt %) in Toluene or Methyl-tert-butyl ether (MTBE) at 45° C.

An 8-mL reaction vial equipped with a stirring bar and containing 200 mg of enzyme, 33 μL DMA, 40 mg of DADD, and 1.93 mL toluene or MTBE, was incubated at 45° C. at constant stirring. Reaction prepared in exactly the same way but without enzyme was performed as non-enzymatic control.

The reactions were analyzed as described in Example 3 except that an approximately 60 μm glass filter was used for filtration of the enzyme. Results are shown in Tables 7 (reactions in toluene) and Table 8 (reactions in MTBE).

TABLE 7

Activity of Various Hydrolytic Enzymes on Macrocylic Amide Synthesis in Toluene

| Trade Name | Enzyme | Source of Enzyme | Supplier | Catalog number | MC % | Solid % | cU % | cD % | CAO % |
|---|---|---|---|---|---|---|---|---|---|
|  | Lipase | *Alcaligenes* sp. | BioCatalytics | ICR-117 | 49 | 1 | 0 | 0 | 0 |
| Chirazyme L10 | Lipase | *Alcaligenes* sp. | Boehringer Mannheim | 1859366 | 44 | 38 | 0 | 0 | 0 |
|  | Lipase | *Candida rugosa* | BioCatalytics | ICR-106 | 5 | 4 | 0 | 0 | 0 |
| Chirazyme L3 | Lipase | *Candida rugosa* | Boehringer Mannheim | 1600885 | 5 | 1 | 0 | 0 | 0 |
|  | Lipase | *Mucor miehei* | BioCatalytics | ICR-116 | 52 | 0 | 0 | 0 | 0 |
| Chirazyme L9 | Lipase | *Mucor miehei* | Boehringer Mannheim | 1831313 | 9 | 0 | 0 | 0 | 0 |
|  | Lipase | *Pseudomonas* sp. | BioCatalytics | ICR-107 | 27 | 0 | 0 | 0 | 0 |
|  | Lipase | *Pseudomonas* sp. | BioCatalytics | ICR-108 | 32 | 0 | 0 | 0 | 0 |
|  | Lipase | *Pseudomonas* sp. | BioCatalytics | ICR-109 | 13 | 0 | 0 | 0 | 0 |
|  | Lipase | *Pseudomonas* sp. | BioCatalytics | ICR-113 | 60 | 0 | 64 | 1.4 | 65.4 |
| Chirazyme L1 | Lipase | *Pseudomonas cepacia* | Boehringer Mannheim | 1827642 | 74 | 7 | 5.7 | 0.5 | 6 |
|  | Lipase | *Rhizopus oryzae* | BioCatalytics | ICR-103 | 0 | 0 | 0 | 0 | 0 |
| Chirazyme L8 | Lipase | *Thermomyces* (*Humicola*) | Boehringer Mannheim | 1625870 | 5 | 0 | 0 | 0 | 0 |
|  | Lipase | *Candida* sp. | BioCatalytics | ICR-III | 0 | 0 | 0 | 0 | 0 |
|  | Lipase | *Burkholderia cepacia* | Amano | PC-C "Amano" I | 0 | 0 | 0 | 0 | 0 |
|  | Lipase | *Burkholderia cepacia* | Amano | PC-C "Amano" II | 20 | 0 | 0 | 0 | 0 |
|  | Lipase | *Burkholderia cepacia* | Amano | PC-D "Amano" I | 21 | 0 | 0 | 0 | 0 |
|  | Lipase | *Candida antartica* A | BioCatalytics | IMB-104 | 0 | 0 | 0 | 0 | 0 |
| Novozym ® 435 | Lipase | *Candida antartica* B | Novozymes | Novozym ® 435 | 100 | 78 | 6.9 | 1.3 | 8.2 |
| Chirazyme L7 | Lipase | Porcine Pancreatic Lipase | Biocatalytics | ICR 114 | 92 | 12 | 0 | 0 | 0 |
|  | Trypsin |  | Fluka | 41145 | 14 | 0 | 0 | 0 | 0 |
|  | α-Chymotrypsin | Bovine, Type II | Sigma | C-4129 | 11 | 0 | 0 | 0 | 0 |
|  | α-Chymotrypsin | Bovine Pancrease | Sigma | C7260 | 10 | 0 | 0 | 0 | 0 |
|  | Protease | *Bacillus* sp. | BioCatalytics | ICR-119 | 18 | 0 | 0 | 0 | 0 |
|  | Esterase | Pig liver | BioCatalytics | ICR-122 | 6 | 0 | 0 | 0 | 0 |
|  | Papain | *Carica papaya* | Fluka | 76221 | 8 | 0 | 0 | 0 | 0 |
|  | NO ENZYME (CONTROL) | N/A | N/A | N/A | 3 | 0 | 0 | 0 | 0 |

N/A = Not applicable.

TABLE 8

Activity of Various Hydrolytic Enzymes on Macrocylic Amide Synthesis in MTBE

| Trade Name | Enzyme | Source of Enzyme | Supplier | Catalog number | MC % | Solid % | cU % | cD % | CAO % |
|---|---|---|---|---|---|---|---|---|---|
|  | Lipase | *Alcaligenes* sp. | BioCatalytics | ICR-117 | 100 | 0 | 1 | 0 | 1 |
| Chirazyme L10 | Lipase | *Alcaligenes* sp. | Boehringer Mannheim | 1859366 | 100 | 0 | 0.9 | 0 | 0.9 |
|  | Lipase | *Candida rugosa* | BioCatalytics | ICR-106 | 0 | 0 | 0 | 0 | 0 |
| Chirazyme L3 | Lipase | *Candida rugosa* | Boehringer Mannheim | 1600885 | 0 | 0 | 0 | 0 | 0 |
|  | Lipase | *Mucor miehei* | BioCatalytics | ICR-116 | 38 | 0 | 1.6 | 0 | 1.6 |
| Chirazyme L9 | Lipase | *Mucor miehei* | Boehringer Mannheim | 1831313 | 0 | 0 | 0 | 0 | 0 |
|  | Lipase | *Pseudomonas* sp. | BioCatalytics | ICR-107 | 64 | 0 | 0 | 0 | 0 |
|  | Lipase | *Pseudomonas* sp. | BioCatalytics | ICR-108 | 41 | 0 | 0 | 0 | 0 |
|  | Lipase | *Pseudomonas* sp. | BioCatalytics | ICR-109 | 45 | 0 | 0 | 0 | 0 |
|  | Lipase | *Pseudomonas* sp. | BioCatalytics | ICR-113 | 100 | 0 | 56 | 3.2 | 59.2 |
| Chirazyme L1 | Lipase | *Pseudomonas cepacia* | Boehringer Mannheim | 1827642 | 100 | 0 | 6.2 | 0.6 | 6.8 |
|  | Lipase | *Rhizopus oryzae* | BioCatalytics | ICR-103 | 0 | 0 | 0 | 0 | 0 |
| Chirazyme L8 | Lipase | *Thermomyces* (*Humicola*) | Boehringer Mannheim | 1625870 | 4 | 0 | 0 | 0 | 0 |
|  | Lipase | *Candida* sp. | BioCatalytics | ICR-III | 11 | 0 | 0 | 0 | 0 |
|  | Lipase | *Burkholderia cepacia* | Amano | PC-C "Amano" I | 0 | 0 | 0.9 | 0 | 0.9 |
|  | Lipase | *Burkholderia cepacia* | Amano | PC-C "Amano" II | 74 | 0 | 1.2 | 0 | 1.2 |
|  | Lipase | *Burkholderia cepacia* | Amano | PC-D "Amano" I | 67 | 0 | 0 | 0 | 0 |
|  | Lipase | *Candida antartica* A | BioCatalytics | IMB-104 | 7 | 0 | 0 | 0 | 0 |

TABLE 8-continued

Activity of Various Hydrolytic Enzymes on Macrocylic Amide Synthesis in MTBE

| Trade Name | Enzyme | Source of Enzyme | Supplier | Catalog number | MC % | Solid % | cU % | cD % | CAO % |
|---|---|---|---|---|---|---|---|---|---|
| Novozym ® 435 | Lipase | *Candida antartica* B | Novozymes | Novozym ® 435 | 100 | 60 | 30.9 | 2 | 32.9 |
| | Trypsin | | Fluka | 41145 | 12 | 0 | 0 | 0 | 0 |
| | α-Chymotrypsin | Bovine, Type II | Sigma | C-4129 | 5 | 0 | 0 | 0 | 0 |
| | α-Chymotrypsin | Bovine Pancrease | Sigma | C7260 | 11 | 0 | 0 | 0 | 0 |
| | Protease | *Bacillus* sp. | BioCatalytics | ICR-119 | 7 | 5 | 0 | 0 | 0 |
| | Esterase | Pig liver | BioCatalytics | ICR-122 | 14 | 0 | 0 | 0 | 0 |
| | Papain | Carica papaya | Fluka | 76221 | Na | 0 | 0 | 0 | 0 |
| | NO ENZYME (CONTROL) | N/A | N/A | N/A | 10 | 0 | 0 | 0 | 0 |

N/A = Not applicable.

Example 9

Synthesis of Macrocyclic Amides from Various Aliphatic Diamines (0.5M) and Diesters (0.5M) with Novozym®) 435 (10 wt %) in Toluene at 70° C.

Dimethyl oxalate (C2 diester), dimethyl malonate (C3 diester), dimethyl succinate (C4 diester), dimethyl adipate (C6 diester), dimethyl suberate (C8 diester), or dimethyl sebacate (C10 diester) and ethylene diamine (C2 diamine), 1,3-diaminopropylene (C3 diamine), 1,10-diaminodecane (C10 diamine), or 1,12-diaminododecane (C12 diamine) were used for cyclic amide oligomer formation. An 8-mL reaction vial equipped with a stirring bar and containing 200 mg of Novozym® 435, selected amounts of diamine, diester, and toluene (Table 9), and 200 mg of 4A molecular sieves, was incubated at 70° C. at constant stirring. Reactions prepared in exactly the same way without immobilized enzyme were performed as non-enzymatic controls.

TABLE 9

Amounts of Diester, Diamine, and Toluene in Reactions with Various Aliphatic Diesters and Diamines

| Diester Type | Diester, mg | Diamine Type | Diamine, mg | Toluene, mL |
|---|---|---|---|---|
| C2 | 118.1 | C2 | 60 | 1.82 |
| C6 | 174.2 | C2 | 60 | 1.77 |
| C10 | 230.31 | C2 | 60 | 1.74 |
| C8 | 202.25 | C3 | 84 | 1.71 |
| C10 | 230.31 | C3 | 84 | 1.69 |
| C6 | 174.2 | C10 | 172 | 1.65 |
| C10 | 230.31 | C10 | 172 | 1.63 |
| C2 | 118.1 | C12 | 200 | 1.68 |
| C3 | 132.1 | C12 | 200 | 1.67 |
| C4 | 146.1 | C12 | 200 | 1.65 |
| C6 | 174.2 | C12 | 200 | 1.63 |
| C8 | 202.25 | C12 | 200 | 1.60 |
| C10 | 230.31 | C12 | 200 | 1.57 |

The reactions were analyzed as described in Example 3. Results are shown in Table 10.

TABLE 10

Influence of Aliphatic Diester of Diamine on Macrocyclic Amide Synthesis

| Enzyme Catalyst, wt % | Diester | Diamine | MC, % | Solid, wt % | cU, % | cD, % | cT, % | CAO, % |
|---|---|---|---|---|---|---|---|---|
| 10 | C2 | C2 | 100 | 69 | 42.8 | 1.5 | 0 | 44.3 |
| 0 | C2 | C2 | 100 | 75 | 20.6 | 0 | 0 | 20.6 |
| 10 | C6 | C2 | 100 | 44 | 3 | 17 | 3.5 | 23.5 |
| 0 | C6 | C2 | 100 | 15 | 8.4 | 0.9 | 0 | 9.3 |
| 10 | C10 | C2 | 100 | 71 | 6.7 | 34.1 | 5 | 45.8 |
| 0 | C10 | C2 | 10 | 0 | 0.7 | 0 | 0 | 0.7 |
| 10 | C8 | C3 | 72 | 21 | 3.3 | 7.9 | 0.4 | 11.6 |
| 0 | C8 | C3 | 0 | 15 | 3.2 | 0 | 0 | 3.2 |
| 10 | C10 | C3 | 100 | 33 | 11.2 | 15.1 | 1 | 27.3 |
| 0 | C10 | C3 | 46 | 0 | 1.3 | 0 | 0 | 1.3 |
| 10 | C6 | C10 | 100 | 38 | 29.4 | 2.5 | 0 | 31.9 |
| 0 | C6 | C10 | 65 | 0 | 0 | 0 | 0 | 0 |
| 10 | C10 | C10 | 93 | 53 | 15.4 | 5.9 | 0 | 21.3 |
| 0 | C10 | C10 | 59 | 0 | 1.4 | 0 | 0 | 1.4 |
| 10 | C2 | C12 | 100 | 56 | 1.4 | 17.6 | 0 | 19 |
| 0 | C2 | C12 | 100 | 47 | 2 | 8.7 | 0 | 10.7 |
| 10 | C3 | C12 | 100 | 66 | 23 | 14.6 | 0.5 | 38.1 |
| 0 | C3 | C12 | 76 | 33 | 4.5 | 6.4 | 0 | 10.9 |
| 10 | C4 | C12 | 100 | 28 | 36.6 | 4.9 | 0 | 41.5 |
| 0 | C4 | C12 | — | 0 | 25.3 | 0.7 | 0 | 26 |
| 10 | C6 | C12 | 94 | 38 | 24.6 | 1.1 | 0 | 25.7 |
| 0 | C6 | C12 | 0 | 0 | 0 | 0 | 0 | 0 |
| 10 | C8 | C12 | 96 | 39 | 37.7 | 4.1 | 0 | 41.8 |
| 0 | C8 | C12 | — | — | 0 | 0 | 0 | 0 |

TABLE 10-continued

Influence of Aliphatic Diester of Diamine on Macrocyclic Amide Synthesis

| Enzyme Catalyst, wt % | Diester | Diamine | MC, % | Solid, wt % | cU, % | cD, % | cT, % | CAO, % |
|---|---|---|---|---|---|---|---|---|
| 10 | C10 | C12 | 97 | 59 | 38.6 | 3.1 | 0 | 41.7 |
| 0 | C10 | C12 | 34 | 0 | 0.9 | 0 | 0 | 0.9 |

Example 10

Synthesis of Macrocyclic Amides from DADD (0.5 M) and Dimethyl Malonate (0.5 M) with Selected Enzymes (10 wt %) in Toluene at 70° C.

An 8-mL reaction vial equipped with a stirring bar and containing 200 mg of enzyme (see Table 11), 132 µL dimethyl malonate, 201 mg of DADD, 1.67 mL toluene, and 200 mg of 4A molecular sieves (when used) was incubated at 70° C. at constant stirring. The non-enzymatic control was prepared in exactly the same way but without the enzyme.

The reactions were analyzed as described in Example 8. Results are shown in Table 11.

TABLE 11

Macrocyclic Amide Synthesis Using C3 Diesters

| Enzyme | Sieves, wt % | MC, % | Solid, wt % | cU, % | cD, % | CAO, % |
|---|---|---|---|---|---|---|
| ICR 113 | 0 | 99 | 0 | 67 | 2 | 69 |
| ICR 129 | 10 | 100 | 23 | 0 | 0 | 0 |
| N435 | 10 | 100 | 48 | 15.4 | 3.2 | 18.6 |
| no enzyme | 10 | 92 | 6 | 0 | 0 | 0 |

Example 11

Synthesis of Macrocyclic Amides from Various Diamines (0.5M) and Diesters (0.5M) with Novozym® 435 (10 wt %) in Toluene at 70° C.

An 8-mL reaction vial equipped with a stirring bar and containing 200 mg of Novozym® 435, selected amounts of diamine, diester, toluene (Table 12), and 200 mg of 4A molecular sieves was incubated at 70° C. at constant stirring. Non-enzymatic controls were prepared in exactly the same way but without immobilized enzyme. Results of the various reactions as shown in Table 13.

TABLE 12

Amounts of Diester, Diamine, and Toluene in Reactions with Various Diesters and Diamines.

| Diester Type | Diester, mg | Diamine Type | Diamine, mg | Toluene, mL |
|---|---|---|---|---|
| Diethyl Adipate | 202 | C12 | 200 | 1.98 |
| Bis(2-butoxyethyl) adipate | 364 | C12 | 200 | 1.44 |
| C10 | 230 | Triethyleneglycol diamine | 200 | 1.57 |
| C10 | 230 | Bis(hexamethylene) triamine | 215 | 1.56 |
| C6 | 174.2 | o-PD | 108 | 1.71 |
| C10 | 202.25 | o-PD | 108 | 1.69 |

The reactions were analyzed as described in Example 2. Results are shown in Table 13.

TABLE 13

Cyclic Amide Oligomer Synthesis Using Various Diesters and Diamines

| Enzyme Catalyst, wt % | Diester | Diamine | MC, % | Solid, wt % | cU, % | cD, % | CAO, % |
|---|---|---|---|---|---|---|---|
| 10 | Diethyl adipate | C12 | 87 | 85 | 11.1 | 0.8 | 11.9 |
| 0 | Diethyl adipate | C12 | 67 | 2 | 0 | 0 | 0 |
| 10 | Bis(2-butoxyethyl) adipate | C12 | 100 | 40 | 49.7 | 4 | 53.7 |
| 0 | Bis(2-butoxyethyl) adipate | C12 | 58 | 2 | 0 | 0 | 0 |
| 10 | C10 | Triethyleneglycol-diamine | 91 | 27 | 16.8 | 206 | 37.4 |
| 0 | C10 | Triethyleneglycol-diamine | 55 | 7 | 0 | 0 | 0 |

TABLE 13-continued

Cyclic Amide Oligomer Synthesis Using Various Diesters and Diamines

| Enzyme Catalyst, wt % | Diester | Diamine | MC, % | Solid, wt % | cU, % | cD, % | CAO, % |
|---|---|---|---|---|---|---|---|
| 10 | C10 | Bis(hexamethylene) triamine | 81 | 28 | 26.5 | 0 | 26.5 |
| 0 | C10 | Bis(hexamethylene) triamine | 84 | 2 | 0 | 0 | 0 |
| 10 | C6 | o-PD | 100 | 8 | 21.4 | 0 | 21.4 |
| 0 | C6 | o-PD | 59 | 0 | 6.6 | 3.4 | 10 |
| 10 | C10 | o-PD | 10 | 6 | 45.1 | 0 | 45.1 |
| 0 | C10 | o-PD | 0 | 0 | 9.6 | 0 | 9.6 |

Example 12

Synthesis of Macrocyclic Amide from 2,2'-(Ethylenedioxy)bis(ethylamine) and Dimethyl Terephthalate with *Candida antartica* lipase B (Chirazyme™ L-2, c-f) in Toluene at 60° C.

A 600-mL filter reactor equipped with a stirring bar and containing 20 g *Candida antartica* lipase B (CHIRAZYME™ L-2, c-f C2, lyo (ID #2207257 Biocatalytics, Pasadena Calif.)), 7.5 g dimethyl terephthalate (0.0386 moles), 22.8 g 2,2'-(ethylenedioxy)bis(ethylamine) (also known as triethyleneglycoldiamine; Jeffamine® EDR-148; CAS 929-59-9; Aldrich catalog # 38,550-6) (0.1538 moles), and 500 mL toluene, was incubated at 60° C. in an oil-heating bath with constant stirring. After 7 days, when according to LC-MS (see below), all DMT was consumed, the reactor was drained through the bottom filter frit leaving enzyme in the reactor, precipitate formed in the drained liquid (3.96 g after drying in vacuum oven) was separated by #1 filter paper, and the filtrate was dried in vacuum oven.

Acetonitrile was added to the dried filtrate, the sample was heated at 50° C. for 15 minutes, and the resulting hazy solution was filtered through a 0.45 micron filter (Acrodisc® CR 25 mm syringe filter, Gelman Laboratory) into a liquid chromatograph sample vial. Analysis (LC/MS) was carried out using a Hewlett-Packard® 1100 Liquid Chromatograph (Agilent Technologies, Palo Alto, Calif.) equipped with a HP G1315A UV Diode array detector and a HP G1946A Mass Spectrometer detector (Agilent Technologies). Two PLgel 50 Angstrom columns (Agilent Technologies) were utilized with $CHCl_3$ as the eluant at a rate of 1 mL/min. Cyclic dimer (mw=556 Da) with a retention time of 13.1 min was identified via mass chromatography along with short linear oligomers. Concentration of cyclic dimer in the mixture containing linear oligomers was determined as 80 mol % via area percent calculations. A reaction carried out in a similar way but without presence of enzyme was run as a control and yielded no cyclic or linear amide oligomers.

Example 13 (Prophetic)

Conversion of Linear Oligomers to Cyclic Oligomers in the Presence of Lipase

The purpose of this example is to show formation of cyclic oligomers from a mixture of linear oligomers in the presence of an enzyme catalyst having cyclic amide oligomer forming activity.

An 8-mL reaction vial equipped with a stirring bar and containing 200 mg of *Candida antartica* lipase B (Novozym® 435), 200 mg of molecular sieves 3A, 157 mg of linear Nylon 12,6 with an average of 10 monomer units in the chain ($M_n$=3132 Da), and 20 µL methanol are suspended in 1.843 mL toluene and incubated at 60° C. for 7 days. An analogous reaction, but in methyl-tert-butyl ether (MTBE), is performed at 45° C. Reactions are prepared in exactly the same way but without enzyme are performed in both solvents at respective temperatures as non-enzymatic controls.

The reactions are analyzed as described in Example 8. The enzymatic reactions are expected to yield cyclic amide oligomers, while non-enzymatic reactions are expected to produce no cyclic oligomers.

Example 14 (Prophetic)

Conversion of Linear Oligomers to Cyclic Oligomers with Addition of Diamine in the Presence of Lipase The purpose of this example is to show formation of cyclic oligomers from a mixture of linear oligomers and diamine in the presence of a hydrolytic enzyme with transamidase and cyclic amide oligomer forming activity.

An 8-mL reaction vial equipped with a stirring bar and containing 200 mg of *Candida antartica* lipase B (Novozym® 435), 200 mg of molecular sieves 3A, 157 mg of linear Nylon 12,6 with an average of 10 monomer units in the chain ($M_n$=3132 Da), and 20 µL methanol are suspended in 1.843 mL toluene and incubated at 60° C. After 3 days, 50 mg DADD is added and the reaction is continued for 7 more days.

The reactions are analyzed as described in Example 8. The enzymatic reactions are expected to yield cyclic amide oligomers, while non-enzymatic reactions are expected to produce no cyclic oligomers.

Example 15 (Prophetic)

Conversion of Linear Oligomers to Cyclic Oligomers with Addition of Diester in the Presence of Lipase The purpose of this example is to show formation of cyclic oligomers from a mixture of linear oligomers and diester in the presence of a hydrolytic enzyme having cyclic amide oligomer forming activity.

An 8-mL reaction vial equipped with a stirring bar and containing 200 mg of *Candida antartica* lipase B (Novozym® 435), 200 mg of molecular sieves 3A, 157 mg of linear Nylon 12,6 with an average of 10 monomer units in the chain ($M_n$=3132 Da), and 20 µL methanol are suspended in 1.843 mL toluene and incubated at 60° C. After 3 days, 43.5 µL dimethyl adipate is added and the reaction is continued for 7 more days.

The reactions are analyzed as described in Example 8. The enzymatic reactions are expected to yield cyclic amide oligomers, while non-enzymatic reactions are expected to produce no cyclic oligomers.

What is claimed is:

1. A process for the enzymatic production of cyclic amide oligomers comprising the steps of:
    (a) contacting,
        i) at least one diester of the general formula

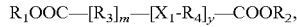
    $R_1OOC—[R_3]_m—[X_1-R_4]_y—COOR_2$, wherein $R_1$ and $R_2$ are independently a C1 to C20 hydrocarbyl group selected from one of alkyl, alkylene, aryl, haloaryl, aralkyl, aralkylene, arylene, alkoxyalkyl, and alkenyl, optionally substituted with one or more ether linkages; $R_3$ and $R_4$ are independently C1 to C10 hydrocarbyl group selected from one of alkyl, alkylene, aryl, haloaryl, aralkyl, aralkylene, arylene, and alkenyl; $X_1$ is selected from one or none of heteroatom or non-heteroatom, wherein the heteroatom comprises oxygen, and wherein the non-heteroatom comprises NH; y is 0 to 5; and m=0 or 1, wherein m is 1 when $X_1$ is a heteroatom or non-heteroatom; and
        (ii) at least one diamine of the general formula

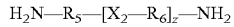
    $H_2N—R_5—[X_2—R_6]_z—NH_2$ wherein $R_5$ and $R_6$ are C1 to C6 hydrocarbyl group selected from the group consisting of alkyl, akylene, aryl, haloaryl, aralkyl, aralkylene, alkarylene, arylene, and alkenyl; $X_2$ is selected from one or none of heteroatom or non-heteroatom, wherein the heteroatom comprises oxygen or sulfur, and wherein the non-heteroatom comprises amine, carbonyl, or C1 to C6 hydrocarbyl group selected from one of alkyl, alkylene, aryl, haloalkyl, aralkyl, aralkylene, arylene or alkenyl; z is from 0 to 20; and
    wherein $R_5$ and $R_6$ may be the same or different;
    under a set of suitable reaction conditions, in a medium comprised of at least one aprotic organic solvent, and in the presence of a lipase having a cyclic amide oligomer synthesizing activity and present in an amount of at least about 0.01% by weight based on the total weight of the diester and diamine whereby a cyclic amide oligomer is produced;
    (b) recovering an amount of cyclic amide oligomer from the reaction of step (a).

2. The process of claim 1 wherein $R_1$ and $R_2$ are independently a C1 to C6 hydrocarbyl group optionally substituted with one or more ether linkages; m is 0 or 1; $R_3$ is C1 to C10 hydrocarbyl group; y is 0 to 5; $R_4$ is a C1 to C3 hydrocarbyl group; $R_5$ and $R_6$ are independently C1 to C6 hydrocarbyl group; z is 0 to 5; and $X_2$ is one or none of heteroatom or non-heteroatom, wherein the heteroatom comprises oxygen or sulfur, and wherein the non-heteroatom comprises amine, carbonyl, or C1 to 4 hydrocarbyl group.

3. The process of claim 2 wherein $R_1$ and $R_2$ are independently a C1 to C6 alkyl group optionally substituted with one or more ether linkages; m is 1; $R_3$ is C1 to C10 alkyl group; y is 0; $R_5$ and $R_6$ are independently is C1 to C6 hydrocarbyl group; z is 0 to 4; and $X_2$ is one or none of heteroatom or non-heteroatom, wherein the heteroatom comprises oxygen or sulfur, and wherein the non-heteroatom comprises amine, carbonyl, or C1 to 4 hydrocarbyl group.

4. The process of claim 3 wherein $R_1$ and $R_2$ are independently a C1 to C6 alkyl group optionally substituted with an ether linkage; m is 1; $R_3$ is C1 to C10 alkyl group; y is 0; $R_5$ is C1 to C6 hydrocarbyl group; z is 0 to 4; $R_6$ is a C1 to C4 alkyl group; $X_2$ is one or none of heteroatom or non-heteroatom, wherein the heteroatom is oxygen, and wherein the non-heteroatom is amine or C1 to C4 alkyl group.

5. The process of claim 4 wherein $R_1$ and $R_2$ are independently a C1 to C2 alkyl group; m is 1; $R_3$ is C1 to C10 alkyl group; y is 0; $R_5$ is C1 to C6 alkyl group; z is 1; $R_6$ is a C1 to C4 alkyl group; and $X_2$ is C1 to C2 alkyl group.

6. The process of claim 1 wherein the aprotic organic solvent is selected from the group consisting of o-dichlorobenzene, diphenyl ether, chlorobenzene, methyl-tert-butyl ether, di-isopropyl ether, tetrahydrofuran, acetone, acetonitrile, 1,4-dioxane, N,N-dimethylfomiamide, dimethyl sulfoxlde, 1,1,1-trichloroethane, dichloroethane, toluene, xylenes, cyclohexane, heptane, isooctane, perobloroethylene, a molar excess of the diamine, a molar excess of the diester, and mixtures thereof.

7. The process of claim 6 wherein the aprotic organic solvent is selected from the group consisting of diphenyl ether, methyl-tert-butyl ether, toluene, a molar excess of the diamine, a molar excess of the diester, and mixtures thereof.

8. The process of claim 7 wherein the aprotic organic solvent is selected from the group consisting of diphenyl ether, methyl-tert-butyl ether, toluene, and mixtures thereof.

9. The process of claim 1 wherein the lipase is from about 0.01% to 25% by weight based on the total weight of the diester and diamine.

10. The process of claim 9 wherein the lipase is unimmobilized or immobilized.

11. The process of claim 10 wherein the lipase is obtained from a natural source or a synthetic source.

12. The process of claim 11 wherein the natural source comprises plants, animals, bacteria, yeast, or fungi.

13. The process of claim 12 wherein the natural source is selected from the group consisting of *Pseudomonas, Burkholderie, Mucor, Alcaligenes*, and *Candida*.

14. The process of claim 13 wherein the natural source is selected from the group consisting of *Alcaligenes* sp., *Mucor miehei, Psoudomonas* sp., *Pseudomonas cepacia, Burkolderia cepacia*, and *Candida antartica*.

15. The process of claim 14 wherein the natural source is selected from the group consisting of *Candida antartica, Pseudmonas* sp., *Pseudomonas cepacia*, and *Burkholderia cepacia*.

16. The process of claim 15 wherein the lipase is selected from the group consisting of *Candida antartica* lipase B, *Alcaligenes* sp. lipase, *Mucor miehei* lipase, *Pseudomonas* sp. lipase, *Burkholderia cepacia* lipase, and *Pseudomonas cepacia* lipase.

17. The process of claim 16 wherein the lipase is selected from the group consisting of *Candida antartica* lipase B (Novozym® 435), *Candida antartica* lipase B (BioCatalytics Chirazyme™ L-2, c-f), *Alcaligenes* sp. lipase (BioCatalytics ICR-117), *Alcaligenes* sp. lipase (Boehringer Mannheim #1859366),*Mucor miehei* lipase (BioCatalytics ICR-116), *Pseudomonas* sp. lipase (BioCatalytics ICR-113), *Pseudomonas* sp. lipase (BioCatalytics ICR-129), *Burkholderia cepacia* lipase (Amano PS-C Amano I), *Burkholderia cepacia* lipase (Amano PS-C Amano II), *Pseudomonas cepacia* lipase (Boehringer Mannheim #1827642), and mixtures thereof.

18. The process of claim 1 wherein the concentration of the diester and/or diamine is less than about 2.5 molar.

19. The process of claim 18 wherein the concentration of the diester and/or diamine is less than about 1.5 molar.

20. The process of claim 19 wherein the concentration of the diester and/or the diamine is about 0.5 molar or less, less than about 1.5 molar.

21. The process of claim 1 or claim 2 wherein the diester is selected from the group consisting of dialkyl adipate, dialky malonate, dialkyl succinate, dialkyl glutarate, dialkyl phthalate, dialkyl isophthalate, dialkyl terephthalate, dialkyl maleate, dialkyl fumarate, dialkyl oxalate, dialkyl phenylmalonate, dialkyl suberate, dialkyl sebacate, bis(2-butoxyethyl) adipate, and mixtures thereof.

22. The process of claim 1 or claim 2 wherein the diamine is selected from the group consisting of 1,6-diaminohexane, 1,12-diamino dodecane, 1,10-diaminodecane, diethylenetriamine, triethyleneglycol diamine, ethylenediamine, propylenediamine, triethytenetetramine, dipropylenetriamine, tripropylenetetramine, tetrapropylenepentamine, spermine, bis-(hexamethylenetriamine), o-phenylenediamine, poly(oxyethylene)diamine, poly(oxypropylene)diamine, polyetherdiamine, and mixtures thereof.

23. The process of claim 1 wherein the cyclic amide oligomers produced are selected from the group consisting of cyclic poly(ethylene oxalamide), cyclic poly(hexamethylene oxalamide), cyclic poly(decamethylene oxalamide), cyclic poly(dodecamethylene oxalamide), cyclic poly(ethylene fumaramide), cyclic poly(hexamethylene fumaramide), cyclic poly(decamethylene fumaramide), cyclic poly(dodecamethylene fumaramide), cyclic poly(propylene malonamide), cyclic poly(hexamethylene malonamide), cyclic poly(decamethylene malonamide), cyclic poly(dodecamethylene malonamide), cyclic poly(ethylene malolamide), cyclic poly(hexamethylene maleiamide), cyclic poly(decamethylene malolamide), cyclic poly(dodecamethylene maleiamide), cyclic poly(hexamethylene succinamide), cyclic poly(decamethylene succinamide), cyclic poly(dodecamethylene succinamide), cyclic poly(hexamethylene glutaramide), cyclic poly(decamethylene glutaramide), cyclic poly(dodecamethylene glutaramide), cyclic poly(ethylene adipamide), cyclic poly(tetramethylene adipamide), cyclic poly(pentamethylene adipamide), cyclic poly(hexamethylene adipamide), cyclic poly(decamethylene adipamide), cyclic poly(dodecamethylene adipamide), cyclic poly(trimethylhexamethylene adipamide), cyclic poly(o-pheriylene adipamide), cyclic poly(ethylene pimelamide), cyclic poly(hexamethylene pimelamide), cyclic poly(decamethylene pimelamide), cyclic poly(dodecamethylene pimelamide), cyclic poly(propylene suberamide), cyclic poly(hexamethylene suberamide), cyclic poly(decamethylene suberamide), cyclic poly(doclecamethylene suberamide), cyclic poly(ethylene azelamide), cyclic poly(hexamethylene azelamide), cyclic poly(decemethylene azelamide), cyclic poly(dodecamethylene azelamide), cyclic poly(ethylene sebacamide), cyclic poly(hexamethylene sebacamide), cyclic poly(decamethylene sebacamide), cyclic poly(dodecarnethylene sebacamide), cyclic poly(triethyleneglycol sebacamide), cyclic poly(bis-hexamethyleneamine sebacamide), cyclic poly(o-phenylene sebacamide), cyclic poly(bis-cyclohexylrnethane sebacamide), cyclic poly(ethylene dodecanediamide), cyclic poly(hexamethylene dodecanediamide), cyclic poly(decamethylene dodecanediamide), cyclic poly(dodecamethylene dodecanediamide), cyclic poly(triethyleneglycol dodecanediamide), cyclic poly(biss-hexamethyleneamine dodecanediamide), cyclic poly(bis-cyclohexlmethane dodecanediamide), cyclic poly(o-phenylene dodecanediamide), cyclic poly(p-phenylene terephthalamide), cyclic poly(m-phenylene terephthalamide), cyclic poly(o-phenylene terephthalamlde), cyclic poly(p-phenylene isophthalamide), cyclic poly(m-phenylene isophthalamide), cyclic poly(o-phenylene isophthalamide), cyclic poly(p-phenylene phthalamide), cyclic poly(m-phenylene phthalamide), cyclic poly(o-phenylene phthalamide), cyclic poly(bis-cyclohexylmethane terephthalamide), cyclic poly(bis-cyclohexylmethane terephthalamide), cyclic poly(bis-cyclohexylemethane terephthalamide), cyclic poly(tnmethylhexamethylene terephthalamide), cyclic poly(trimethylhexamethylene isophthalamide), cyclic poly(trimethylhexamethylene phthalamide), cyclic poly(hexamethylene terephthalamide), cyclic poly(decamethylene terephthalamide), cyclic poly(dodecamethylene terephthalamide), cyclic poly(triethyleneglycol terephthalamide), cyclic poly(bis-hexamethyleneamine terephthalamide), cyclic poly(hexamethylene phthalamide), cyclic poly(decamethylene phthalamide), cyclic poly(dodecamethylene phthalamide), cyclic poly(triethyleneglycol phthalamide), cyclic poly(bis-hexamethyleneamine phthalamide), cyclic poly(hexamethylene isophthalamide), cyclic poly(decamethylene isophthalamide), cyclic poly(dodecamethylene isophthalamide), cyclic poly(triethyleneglycol isophthalamide), and cyclic poly(bis-hexamethylene amine isophthalamide).

24. The process of claim 23 wherein the cyclic amide oligomers produced are selected from the group consisting of cyclic poly(ethylene oxalamide), cyclic poly(hexamethylene oxalamide), cyclic poly(decamethyiene oxalamide), cyclic poly(dodecamethylene oxalamide), cyclic poly(ethylene fumaramide), cyclic poly(hexamethylene fumaramide), cyclic poly(decamethylene fumaramide), cyclic poly(dodecamethylene fumaramide), cyclic poly(propylene malonamide), cyclic poly(hexamethylene malonamide), cyclic poly(decamethylene malonamide), cyclic poly(dodecamethylene malonamide), cyclic poly(ethylene malelamide), cyclic poly(hexamethylene malelamide), cyclic poly(decamethylene maleiamide), cyclic poly(dodecamethyiene maleiamide), cyclic poly(hexamethylene succinamide), cyclic poly(decamethylene succinamide), cyclic poly(dodecamethylene succinamide), cyclic poly(hexamethylene glutaramide), cyclic poly(decamethylene glutaramide), cyclic poly(dodecamethylene glutaramide), cyclic poly(ethylene adipamide), cyclic poly(tetramethylene adipamide), cyclic poly(pentamethylene adipamide), cyclic poly(hexamethylene adipamide), cyclic poly(decamethylene adipamide), cyclic poly(dodecamethylene adipamide), cyclic poly(trimethylhexamethylene adipamide), cyclic poly(o-phenylene adipamide), cyclic poly(ethylene pimelamide), cyclic poly(hexamethylene pimelamide), cyclic poly(decamethylene pimelamide), cyclic poly(dodecamethylene pimelamide), cyclic poly(propylene suberamide), cyclic poly(hexamethylene suberamide), cyclic poly(decamethylene suberamide), cyclic poly(dodecamethylene suberamide), cyclic poly(ethylene azelamide), cyclic poly(hexamethylene azelamide), cyclic poly(decamethylene azelamide), cyclic poly(dodecamethylene azelamide), cyclic poly(ethylene sebacamide), cyclic poly(hexamethylene sebacamide), cyclic poly(decamethylene sebacamide), cyclic poly(dodecamethylene sebacamide), cyclic poly(triethyleneglycol sebacamide), cyclic poly(bis-hexamethyleneamine sebacamide), cyclic poly(o-phenylene sebacamide), cyclic poly(bis-cyclohexylmethane sebacamide), cyclic poly(ethylene dodecanediamide), cyclic poly(hexamethylene dodecanediamide), cyclic poly(decamethylene dodecanediamide), cyclic poly(doclecamethylene dodecanediamide), cyclic poly(triethyleneglycol dodecanediamide), cyclic poly(bis-hexamethyleneamine dodecanediamide), cyclic poly(bis-cyclohexylmethane dodecanediamide), cyclic poly(o-phenylene dodecanediamide), cyclic poly(p-phenylene terephthalamide), cyclic poly(m-phenylene terephthalamide), cyclic poly(o-phenylene terephthalamide), cyclic poly(p-phenylene isophthalamide), cyclic poly(m-phenylene isophthalamide), cyclic poly(o-phenylene isophthalamide), cyclic poly(p-phenylene phthalamide), cyclic poly(m-phenylene phthalamide), cyclic poly(o-phenylene phthalamide), cyclic poly(bis-cyclohexylmethane terephthalamide), cyclic poly(bis-cyclohexylmethane terephthalamide), cyclic poly(bis-cyclohexylemethane terephthe lamide), cyclic poly(trimethylhexamethylene terephthalamide), cyclic poly(trimethylhexamethylene isophthalamide), cyclic poly(trimethylhexamethylene phthalamide), cyclic poly(hexamethylene terephthalamide), cyclic poly(docamethylene terephthalamide), cyclic poly(dodecamethylene terephthalamide), cyclic poly(triethyleneglycol terephthalamide), cyclic poly(bis-hexamethyleneamine terephthalamide), cyclic poly(hexamethylene phthalamide), cyclic poly(decamethylene phthalamide), cyclic poly(dodecamethylene phthalamide), cyclic poly(triethyleneglycol phthalamide), cyclic poly(bis-hexamethyleneamine phthalamide), cyclic poly(hexarnethylene isophthalamide), cyclic poly(decamethylene isophthalamide), cyclic poly(dodecamethylene isophthalamide), cyclic poly(triethyleneglycol isophthalamide), and cyclic poly(bis-hexamethylene amine isophthalamide).

25. The process of claim 24 wherein the cyclic amide oligomer is cyclic poly(hexamethylene adipamide).

26. The process of claim 24 wherein the cyclic amide oligomer is cyclic poly(dodecamethylene adipamide).

27. The process of claim 1, 2, 3, 4, 5, 23, 24, 25 or 26 wherein the cyclic amide oligomer is produced at a concentration of at least 1 mole percent.

28. The process of claim 27 wherein the cyclic amide oligomer is produced at a concentration of at least 5 mole percent.

29. The process of claim 28 wherein the cyclic amide oligomer is produced at a concentration of at least 25 mole percent.

30. The process of claim 1 wherein the cyclic amide oligomers have a degree of polymerization from 1 to about 20.

31. The process of claim 30 wherein the cyclic amide oligomers have a degree of polymerization from 1 to about 5.

32. The process of claim 31 wherein the cyclic amide oligomers have a degree of polymerization from 1 to about 3.

33. The process of claim 1 wherein the suitable reaction conditions comprises a reaction temperature of about 0° C. to about 130° C.

34. The process of claim 33 wherein the suitable reaction conditions comprises a reaction temperature of about 40° C. to about 75° C.

35. The process of claim 33 or 34 wherein the suitable reaction conditions includes molecular sieves.

36. The process of claim 35 wherein the molecular sieves has an average pore diameter of about 3 or about 4 angstroms, conditions includes molecular sieves.

37. A process for the enzymatic production of cyclic amide oligomers comprising the steps of:
(a) contacting, in the presence of a lipase having a cyclic amide oligomer synthesizing activity under a set of suitable reaction conditions, at least one linear amide oligomer of the general formula:

(A-B)$_n$ wherein n=1 to 20; A is derived from a diester having the general formula:

R$_1$OOC—[R$_3$]$_m$—[X$_1$—R$_4$]$_y$—COOR$_2$, wherein R$_1$ and R$_2$ are independently C1 to C20 hydrocarbyl group selected from one of alkyl, alkylene, aryl, haloaryl, aralkyl, aralkylene, arylene, alkoxyalkyl, and alkenyl, optionally substituted with one or more ether linkages; R3 and R4 are independently C1 to C10 hydrocarbyl group selected from one of alkyl, alkylene, aryl, haloaryl, aralkyl, aralkylene, arylene, and alkenyl; X$_1$ is selected from one or none of heteroatom or non-heteroatom, wherein the heteroatom comprises oxygen, and wherein the non-heteroatom comprises NH; m is 0 or 1; and y is 0 to 5; wherein m is 1 when X$_1$ is a heteroatom or non-heteroatom, and B is derived from a diamine having the general formula:

H$_2$N—R$_5$—[X$_2$—R$_6$]$_z$—NH$_2$;

wherein R$_5$ and R$_6$ are C1 to C6 hydrocarbyl group selected from tile group consisting of alkyl, akylene, aryl, haloaryl, aralkyl, aralkylene, elkarylene, arylene, and alkenyl; X$_2$ is selected from one or none of heteroatom or non-heteroatom, wherein the heteroatom comprises oxygen or sulfur, and wherein the non-heteroatom comprises amine, carbonyl, or C1 to C6 hydrocarbyl group selected from one of alkyl, alkylene, aryl, haloalkyl, aralkyl, aralkylene, arylene or alkenyl; z is from 0 to 20; and wherein R$_5$ and R$_6$ may be the same or different;
under a set of suitable reaction conditions, in a medium comprised of at least one aprotic organic solvent, in the presence of a lipase having a cyclic amide oligomer synthesizing activity and present in an amount of at least about 0.01% by weight based on the total weight of the diester and diamine, whereby a cyclic amide oligomer is produced;
(b) recovering an amount of cyclic amide oligomer from the reaction of step (a).

38. The process of claim 37 wherein the aprotic organic solvent is selected from the group consisting of o-dichlorobenzene, diphenyl ether, chlorobenzene, methyl-tert-butyl ether, di-isopropyl ether, tetrahydrofuran, acetone, acetonitnie, 1,4dioxane, N,N-dimethylformamide, dimethyl suffoxide, 1,1,1-trichioroethane, dichioroethane, toluene, xylenes, cyclohexane, heptane, isooctane, perchloroethylene, a molar excess of diamine, a molar excess of diester, and mixtures thereof.

39. The process of claim 38 wherein the aprotic organic solvent is selected from the group consisting of diphenyl ether, methyl-tert-butyl ether, toluene, a molar excess of the diamine, a molar excess of the diester, and mixtures thereof.

40. The process of claim 39 wherein the aprotic organic solvent is selected from the group consisting of diphenyl ether, methyl-tert-butyl ether, toluene, and mixtures thereof.

41. The process of claim 37 wherein R$_1$ and R$_2$ are independently a C1 to C6 hydrocarbyl group optionally substituted with one or more ether linkages; m is 0 or 1; R$_3$ is C1 to C10 hydrocarbyl group; y is 0 to 5; R$_4$ is a C1 to C3 hydrocarbyl group: R$_5$ and R$_6$ are independently C1 to C6 hydrocarbyl group; z is 0 to 5; and X$_2$ is one or none of heteroatom or non-heteroatom, wherein the heteroatom comprises oxygen or sulfur, and wherein the non-heteroatom comprises amine, carbonyl, or C1 to 4 hydrocarbyl group.

42. The process of claim 41 wherein R$_1$ and R$_2$ are independently a C1 to C6 alkyl group optionally substituted with one or more ether linkages; m is 1; R$_3$ is C1 to C10 alkyl group; y is 0; R$_5$ and R$_6$ are independently is C1 to C6 hydrocarbyl group; z is 0 to 4; and X$_2$ is one or none of heteroatom or non-heteroatom, wherein the heteroatom comprises oxygen or sulfur, and wherein the non-heteroatom comprises amine, carbonyl, or C1 to 4 hydrocarbyl group.

43. The process of claim 42 wherein R$_1$ and R$_2$ are independently a C1 to C6 alkyl group optionally substituted with an ether linkage; m is 1; R$_3$ is C1 to C10 alkyl group; y is 0; R$_5$ is C$_1$ to C6 hydrocarbyl group; z is 0 to 4; R$_6$ is a C1 to C4 alkyl group; $X_2$ is one or none of heteroatom or non-heteroatom, wherein the heteroatom is oxygen, and wherein the non-heteroatom is amine or C1 to C4 alkyl group.

44. The process of claim 43 wherein $R_1$ and $R_2$ are independently a C1 to C2 alkyl group; m is 1; $R_3$ is C1 to C10 elkyl group; y is 0; $R_5$ is C1 to C6 alkyl group; z is 1; $R_6$ is C1 to C4 alkyl group; and $X_2$ is C1 to C2 alkyl group.

45. The process of claim 37 wherein the tipase is unimmobilized or immobilized.

46. The process of claim 45 wherein the lipase is from about 0.01% to 25% by weight based on the total weight of the diester and diamine.

47. The process of claim 45 wherein the lipase is obtained form a natural or a synthetic source.

48. The process of claim 47 wherein the natural source comprises plants, animals, bacteria, yeast, and fungi.

49. The process of claim 48 wherein the natural source is selected from the group consisting of *Pseudomonas, Burkholderia, Mucor, Alcaligenes*, and *Candida*.

50. The process of claim 49 wherein the source organism for the lipase is selected from the group consisting of *Alcaligenes* sp., *Mucor miehei*, *Pseudomonas* sp., *Pseudomonas cepacia, Burkholderia cepacia*, and *Candida antartica*.

51. The process of claim 50 wherein the natural source is selected from the group consisting of *Candida antartica, Pseudomonas* sp., *Pseudomonas cepacia*, and *Burkholderia cepacia*.

52. The process of claim 51 wherein the lipase is selected from the group consisting of *Candida antartica* lipase B, *Alcaligenes* sp. lipase, *Mucor miehei* lipase, *Pseudomonas* sp. lipase, *Burkholderia cepacia* lipase, and *Pseudomonas cepacia* lipase.

53. The process of claim 52 wherein the lipase is selected from the group consisting of *Candida antartica* lipase B (Novozym® 435), *Candida antartica* lipase B (BioCatalytics Chirazyme™ L-2, c-f), *Alcaligenes* sp. lipase (BioCatalytics ICR-117), *Alcaligenes* sp. lipase (Boehringer Mannheim #1859366), *Mucor miehei* lipase (BioCatalytics ICR-116), *Pseudomonas* sp. lipase (BioCatalytics ICR-113), *Pseudomonas* sp. lipase (BioCatalytics ICR-129), *Burkholderia cepacia* lipase (Amano PS-C Amano I), *Burkholderia cepacia* lipase (Amano PS-C Amano II), *Pseudomonas cepacia* lipase (Boehringer Mannheim #1827642), and mixtures thereof.

54. The process of claim 37 wherein the concentration of the linear amide oligomer is less than about 1 molar.

55. The process of claim 54 wherein the concentration of the linear amide oligomer is less than about 0.3 molar.

56. The process of claim 55 wherein the concentration of the linear amide oligomer is about 0.1 molar or less.

57. The process of claim 37 or 38 wherein the diester is selected from the group consisting of dialkyl adipate, dialkyl malonate, dialkyl succinate, dialkyl glutarate, dialkyl phthalate, dialkyl isophthalate, dialkyl terephthalate, dialkyl maleate, dialkyl fumarate, dialkyl oxalate, dialkyl phenylmalonate, dialkyl suberate, dialkyl sebacate, bis(2-butoxyethyl) adipate, and mixtures thereof.

58. The process of claim 37 or 38 wherein the diamine is selected from the group consisting of 1,6-diaminohexane, 1,12-diamino dodecane, 1,10-diaminodecane, diethylenetriamine, triethyleneglycol diamine, ethylenediamine, propylenediamine, triethylenetetramine, dipropylenetriamine, tripropylenetetramine, tetrapropylenepentamine, spermine, bis-(hexamethylenetriamine), o-phenylenediamine, poly(oxyethylene)diamine, poly(oxypropylene)diamine, polyetherdiamine, and mixtures thereof.

59. The process of claim 37 wherein the cyclic amide oligomers produced are selected from the group consisting of cyclic poly(ethylene oxalamide), cyclic poly(hexamethylene oxalamide), cyclic poly(decamethylene oxalamide), cyclic poly(dodecamethylene oxalamide), cyclic poly(ethylene fumaramide), cyclic poly(hexamethylene fumaramide), cyclic poly(decamethylene fumaramide), cyclic poly (dodecamethylene fumaramide), cyclic poly(propylene malonamide), cyclic poly(hexamethylene malonamide), cyclic poly(decamethylene malonamide), cyclic poly(dodecamethylene malonamide), cyclic poly(ethylene maleiamide), cyclic poly(hexamethylene maleiamide), cyclic poly(decamethylene maleiamide), cyclic poly(dodecamethylene maleiamide), cyclic poly(hexamethylene succinamide), cyclic poly(decamethylene succinamide), cyclic poly(dodecamethylene succinamide), cyclic poly(hexamethylene glutaramide), cyclic poly(decamethylene glutaramide), cyclic poly(dodecamethylene glutaramide), cyclic poly(ethylene adipamide), cyclic poly(tetramethylene adipamide), cyclic poly(pentamethylene adipamide), cyclic poly(hexamethylene adipamide), cyclic poly(decamethylene adipamide), cyclic poly(dodecamethylene adipamide), cyclic poly(trimethylhexamethylene adipamide), cyclic poly(o-phenylene adipamide), cyclic poly (ethylene pimelamide), cyclic poly(hexamethylene pimelamide), cyclic poly(decamethylene pimelamide), cyclic poly (dodecamethylene pimelamide), cyclic poly(propylene suberamide), cyclic poly(hexamethylene suberamide), cyclic poly(decamethylene suberamide), cyclic poly(dodecamethylene suberamide), cyclic poly(ethylene azelamide), cyclic poly(hexamethylene azelamide), cyclic poly(decamethylene azelamide), cyclic poly(dodecamethylene azelamide), cyclic poly(ethylene sebacamide), cyclic poly(hexamethylene sebacamide), cyclic poly(decamethylene sebacamide), cyclic poly(dodecamethylene sebacamide), cyclic poly(triethyleneglycol sebacamide), cyclic poly(bis-hexamethyleneamine sebacamide), cyclic poly(o-phenylene sebacamide), cyclic poly(bis-cyclohexylmethane sebacamide), cyclic poly (ethylene dodecanediamide), cyclic poly(hexamethylene dodecanediamide), cyclic poly(decamethylene dodecanediamide), cyclic poly(dodecamethylene dodecanediamide), cyclic poly(triethyleneglycol dodecanediamide), cyclic poly (bis-hexamethyleneamine dodecanediamide), cyclic poly (bis-cyclohexylmethane dodecanediamide), cyclic poly(o-phenylene dodecanediamide), cyclic poly(p -phenylene terephthalamide), cyclic poly(m-phenylene terephthalamide), cyclic poly(o-phenylene terephthalamide), cyclic poly (p-phenylene isophthalamide), cyclic poly(m-phenylene isophthalamide), cyclic poly(o-phenylene isophthalamide), cyclic poly(p-phenylene phthalamide), cyclic poly(m-phenylene phthalamide), cyclic poly(o-phenylene phthalamide), cyclic poly(bis-cyclohexylmethane terephthalamide), cyclic poly(bis-cyclohexylmethane terephthalamide), cyclic poly (bis-cyclohexylemethane terephthalamide), cyclic poly(trimethylhexamethylene terephthalamide), cyclic poly(trimethylhexamethylene isophthalamide), cyclic poly (trimethylhexamethylene phthalamide), cyclic poly (hexamethylene terephthalamide), cyclic poly (decamethylene terephthalamide), cyclic poly (dodecamethylene terephthalamide), cyclic poly (triethyleneglycol terephthalamide), cyclic poly(bis-hexamethyleneamine terephthalamide), cyclic poly (hexamethylene phthalamide), cyclic poly(decamethylene phthalamide), cyclic poly(dodecamethylene phthalamide), cyclic poly(triethyleneglycol phthalamide), cyclic poly(bis-hexamethyleneamine phthalamide), cyclic poly(hexamethylene isophthalamide), cyclic poly(decamethylene isophthalamide), cyclic poly(dodecamethylene isophthalamide), cyclic poly(triethyleneglycol isophthalamide), and cyclic poly(bis-hexamethylene amine isophthalamide).

60. The process of claim 59 wherein the cyclic amide oligomers produced are selected from the group consisting of cyclic poly(ethylene oxalamide), cyclic poly(hexamethylene oxalamide), cyclic poly(decamethylene oxalamide), cyclic poly(dodecamethylene oxalamide), cyclic poly(ethylene fumaramide), cyclic poly(hexamethylene fumaramide), cyclic poly(decamethylene fumaramide), cyclic poly(dodecamethylene fumaramide), cyclic poly(propylene malonamide), cyclic poly(hexamethylene malonamide), cyclic poly(decamethylene malonamide), cyclic poly(dodecamethylene malonamide), cyclic poly(ethylene maleiamide), cyclic poly(hexamethylene maleiamide), cyclic poly(decamethylene maleiamide), cyclic poly(dodecamethylene maleiamide), cyclic poly(hexamethylene succinamide), cyclic poly(decamethylene succinamide), cyclic poly(dodecamethylene succinamide), cyclic poly(hexamethylene glutaramide), cyclic poly(decamethylene glutaramide), cyclic poly(dodecamethylene glutaramide), cyclic poly(ethylene adipamide), cyclic poly(tetramethylene adipamide), cyclic poly(pentamethylene adipamide), cyclic poly(hexamethylene adipamide), cyclic poly(decamethylene adipamide), cyclic poly(dodecamethylene adipamide), cyclic poly(trimethylhexamethylene adipamide), cyclic poly(o-phenylene adipamide), cyclic poly(ethylene pimelamide), cyclic poly(hexamethylene pimelamide), cyclic poly(decamethylene pimelamide), cyclic poly(dodecamethylene pimelamide), cyclic poly(propylene suberamide), cyclic poly(hexamethylene suberamide), cyclic poly(decamethylene suberamide), cyclic poly(dodecamethylene suberamide), cyclic poly(ethylene azelamide), cyclic poly(hexamethylene azelamide), cyclic poly(decamethylene azelamide), cyclic poly(dodecamethylene azelamide), cyclic poly(ethylene sebacamide), cyclic poly(hexamethylene sebacamide), cyclic poly(decamethylene sebacamide), cyclic poly(dodecamethylene sebacamide), cyclic poly(triethyleneglycol sebacamide), cyclic poly(bis-hexamethyleneamine sebacamide), cyclic poly(o-phenylene sebacamide), cyclic poly(bis-cyclohexylmethane sebacamide), cyclic poly(ethylene dodecanediamide), cyclic poly(hexamethylene dodecanediamide), cyclic poly(decamethylene dodecanediamide), cyclic poly(dodecamethylene dodecanediamide), cyclic poly(triethyleneglycol dodecanediamide), cyclic poly(bis-hexamethyleneamine dodecanediamide), cyclic poly(bis-cyclohexylmethane dodecanediamide), cyclic poly(o-phenylene dodecanediamide), cyclic poly(p-phenylene terephthalamide), cyclic poly(m-phenylene terephthalamide), cyclic poly(o-phenylene terephthalamide), cyclic poly(p-phenylene isophthalamide), cyclic poly(m-phenylene isophthalamide), cyclic poly(o-phenylene isophthalamide), cyclic poly(p-phenylene phthalamide), cyclic poly(m-phenylene phthalamide), cyclic poly(o-phenylene phthalamide), cyclic poly(bis-cyclohexylmethane terephthalamide), cyclic poly(bis-cyclohexylmethane terephthalamide), cyclic poly(bis-cyclohexylemethane terephthalamide), cyclic poly(trimethylhexamethylene terephthalamide), cyclic poly(trimethylhexamethylene isophthalamide), cyclic poly(trimethylhexamethylene phthalamide), cyclic poly(hexamethylene terephthalamide), cyclic poly(decamethylene terephthalamide), cyclic poly(dodecamethylene terephthalamide), cyclic poly(triethyleneglycol terephthalamide), cyclic poly(bis-hexamethyleneamine terephthalamide), cyclic poly(hexamethylene phthalamide), cyclic poly(decamethylene phthalamide), cyclic poly(dodecamethylene phthalamide), cyclic poly(triethyleneglycol phthalamide), cyclic poly(bis-hexamethyleneamine phthalamide), cyclic poly(hexamethylene isophthalamide), cyclic poly(decamethylene isophthalamide), cyclic poly(dodecamethylene isophthalamide), cyclic poly(triethyleneglycol isophthalamide), and cyclic poly(bis-hexamethylene amine isophthalamide).

61. The process of claim 60 wherein the cyclic amide oligomer is cyclic poly(hexamethylene adipamide).

62. The process of claim 60 wherein the cyclic amide oligomer is cyclic poly(dodecamethylene adipamide).

63. The process of claim 37, 41, 42, 43, 61, or 62 wherein the cyclic amide oligomer is produced at a concentration of at least 1 mole percent.

64. The process of claim 63 wherein the cyclic amide oligomer is produced at a concentration of at least 5 mole percent.

65. The process of claim 64 wherein the cyclic amide oligomer is produced at a concentration of at least 25 mole percent.

66. The process of claim 37 wherein the suitable reaction conditions comprises a reaction temperature range of about 0° C. to about 130° C.

67. The process of claim 66 wherein the reaction temperature range is about 40° C. to about 75° C.

* * * * *